United States Patent
Salehi et al.

(10) Patent No.: US 9,320,724 B2
(45) Date of Patent: Apr. 26, 2016

(54) METHOD OF IMPROVING COGNITION AND INCREASING DENDRITIC COMPLEXITY IN HUMANS WITH DOWN SYNDROME AND COMPOSITIONS THEREFOR

(71) Applicants: Ahmad Salehi, Palo Alto, CA (US);
Brian Mediana, Palo Alto, CA (US);
Sarah Moghadam, Palo Alto, CA (US);
Van Dang, Palo Alto, CA (US);
Devsmita Das, Palo Alto, CA (US);
Kara Martin, Palo Alto, CA (US)

(72) Inventors: Ahmad Salehi, Palo Alto, CA (US);
Brian Mediana, Palo Alto, CA (US);
Sarah Moghadam, Palo Alto, CA (US);
Van Dang, Palo Alto, CA (US);
Devsmita Das, Palo Alto, CA (US);
Kara Martin, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/179,088

(22) Filed: Feb. 12, 2014

(65) Prior Publication Data

US 2014/0235726 A1 Aug. 21, 2014

Related U.S. Application Data

(60) Provisional application No. 61/850,309, filed on Feb. 13, 2013.

(51) Int. Cl.
*A61K 31/167* (2006.01)
*A61K 31/138* (2006.01)
*A61P 25/28* (2006.01)
*A61K 45/06* (2006.01)

(52) U.S. Cl.
CPC ............. *A61K 31/167* (2013.01); *A61K 31/138* (2013.01); *A61K 45/06* (2013.01)

(58) Field of Classification Search
CPC .... A61K 31/167; A61K 45/06; A61K 31/138

USPC .................................. 514/630, 652, 653, 657
See application file for complete search history.

(56) References Cited

U.S. PATENT DOCUMENTS

| 6,490,472 B1 | 12/2002 | Li et al. |
| 7,569,586 B2 | 8/2009 | Mammen et al. |
| 2011/0286932 A1 | 11/2011 | Koronyo et al. |

OTHER PUBLICATIONS

Ramos et al. Pharmacol. Ther. 2007, 113 (3), 523-536.*
Lichter et al Br. J. Clin. Pharmacol. 1986, 21, 641-645.*
Das et al. Disease Models & Mechanisms 2011, 4, 596-606.*
Salehi et al. Science Translational Medicine 2009, 1 (7), 7ra17.*
Alford, K.A. et al. (Apr. 8, 2010, e-published Feb. 12, 2010). "Perturbed hematopoiesis in the Tc1 mouse model of Down syndrome," *Blood* 115(14):2928-2937.
Berthault, F. et al. (May-Jun. 1997). "A fatal case of betaxolol poisoning," *J Anal Toxicol* 21(3):228-231.
Edgin, J.O. et al (Sep. 1, 2010). "Development and validation of the Arizona Cognitive Test Battery for Down syndrome," *J Neurodev Disord* 2(3):149-164.
Davisson, M.T. et al. (1993). "Segmental trisomy as a muse model for down syndrome," in *The Phenotypic Mapping of Down Syndrome and Other Aneuploid Conditions*, 1993 Wiley-Liss, Inc. pp. 117-133.
Olson, L.E. et al. (Jul. 2004). Down syndrome mouse models Ts65Dn, Ts1Cje, and Ms1Cje/Ts65Dn exhibit variable severity of cerebellar phenotypes, *Dev Dyn* 230(3):581-589.
Ruparelia, A. et al. (Oct. 2012, e-published May 30, 2012). "Cognitive and pharmacological insights from the Ts65Dn mouse model of Down syndrome," *Curr Opin Neurobiol* 22(5):880-886.

* cited by examiner

*Primary Examiner* — Sreeni Padmanabhan
*Assistant Examiner* — Irina Neagu
(74) *Attorney, Agent, or Firm* — Mintz Levin Cohn Ferris Glovsky and Popeo, P.C.

(57) ABSTRACT

A method of improving cognition in a patient with Down syndrome, which entails administering one or more β2 adrenergic receptor agonists to the patient in an amount and with a frequency effective to improve cognition of the patient as measured by contextual learning tests.

14 Claims, 19 Drawing Sheets

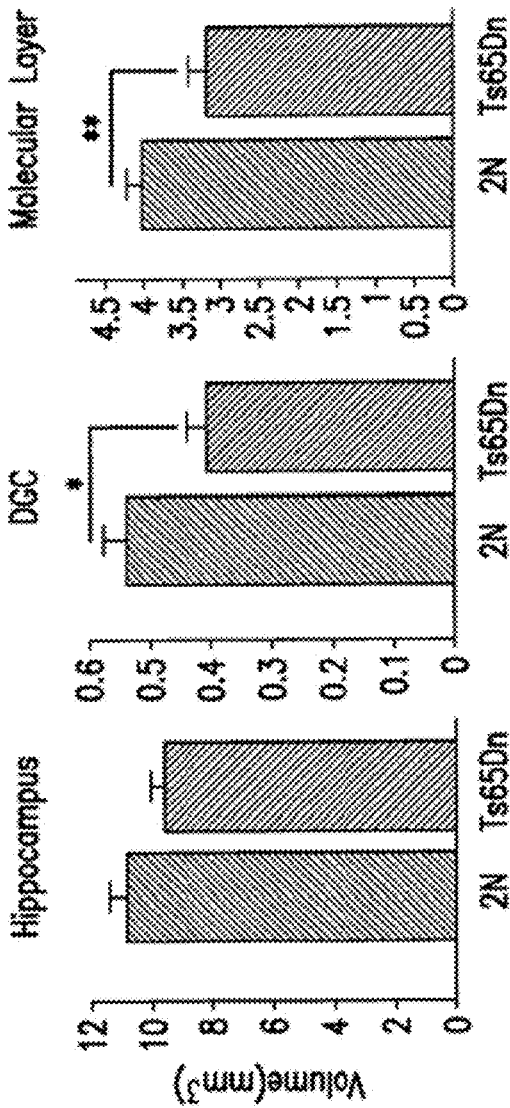
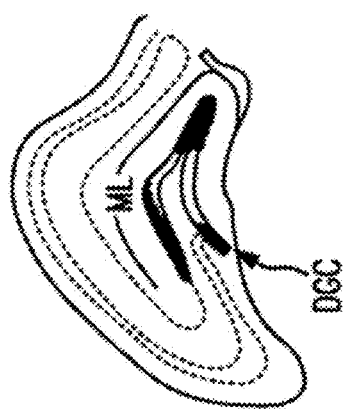
FIG. 1A FIG. 1B FIG. 1C FIG. 1D

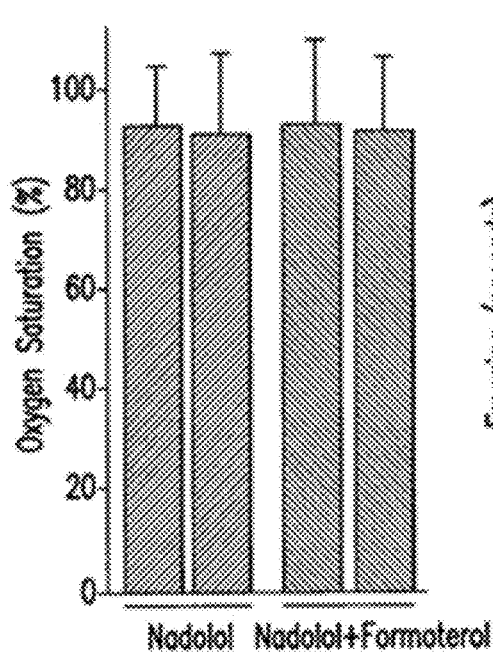
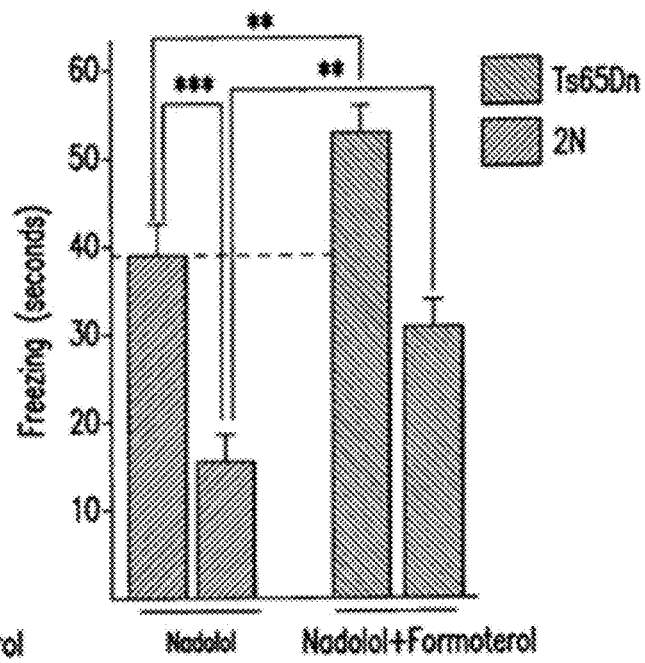
FIG. 4A
FIG. 4B
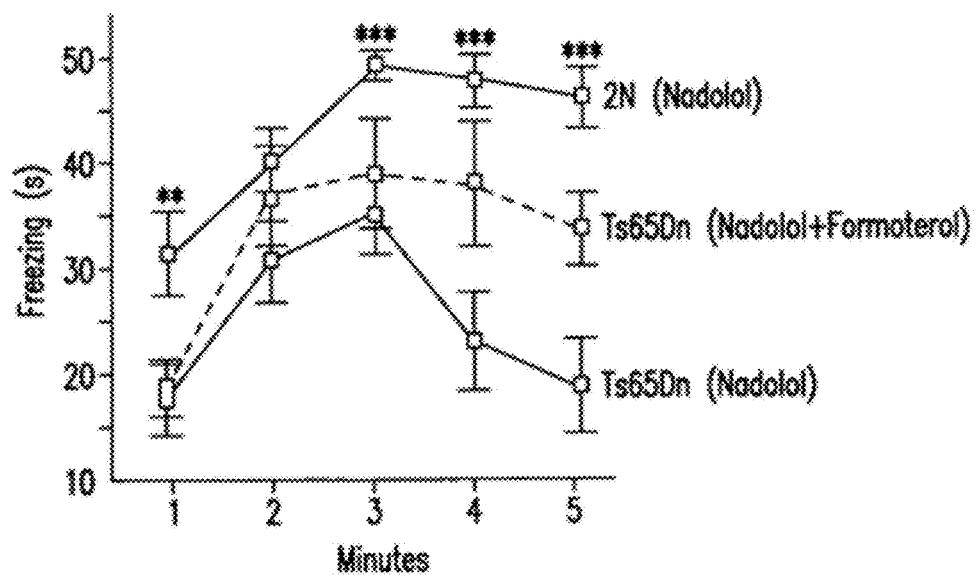
FIG. 4C

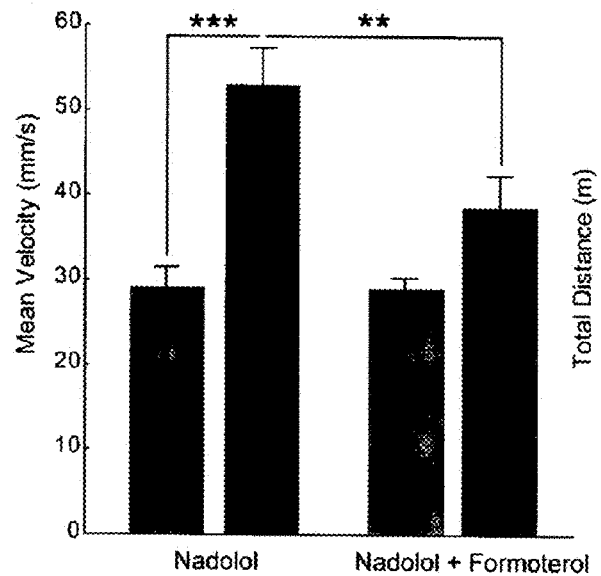
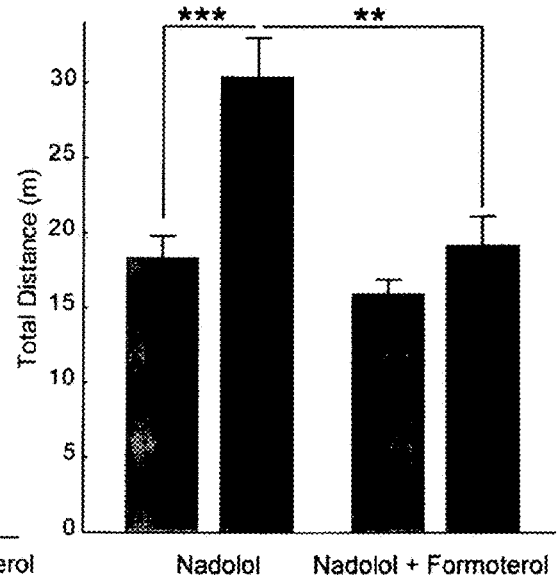
FIG. 5A  FIG. 5B
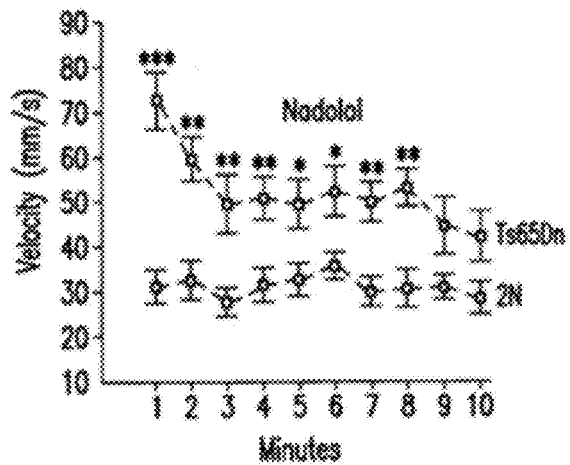
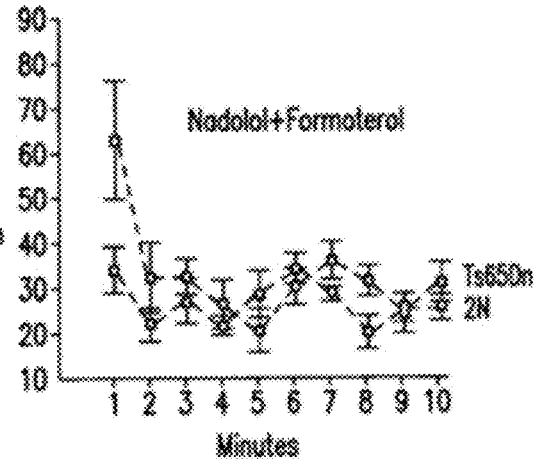
FIG. 5C  FIG. 5D

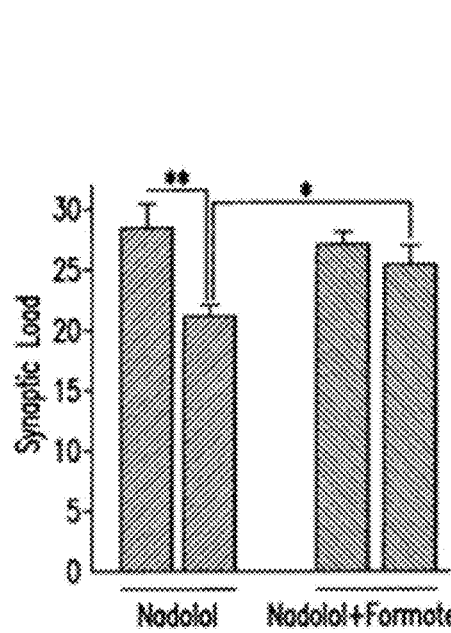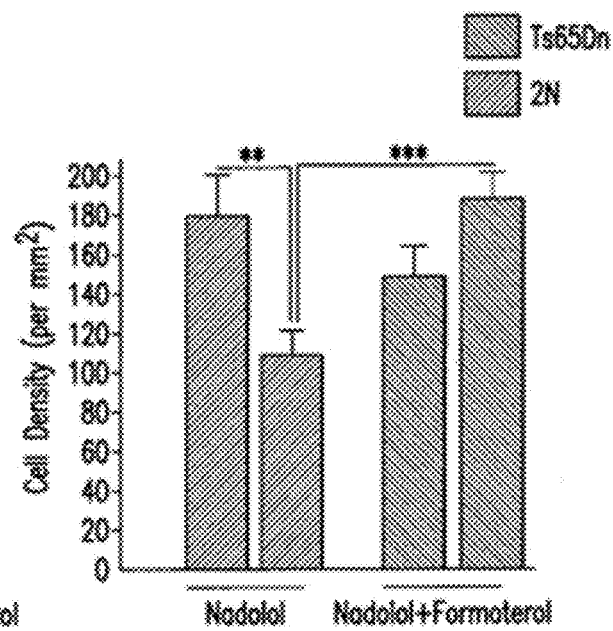
FIG. 6A  FIG. 6B
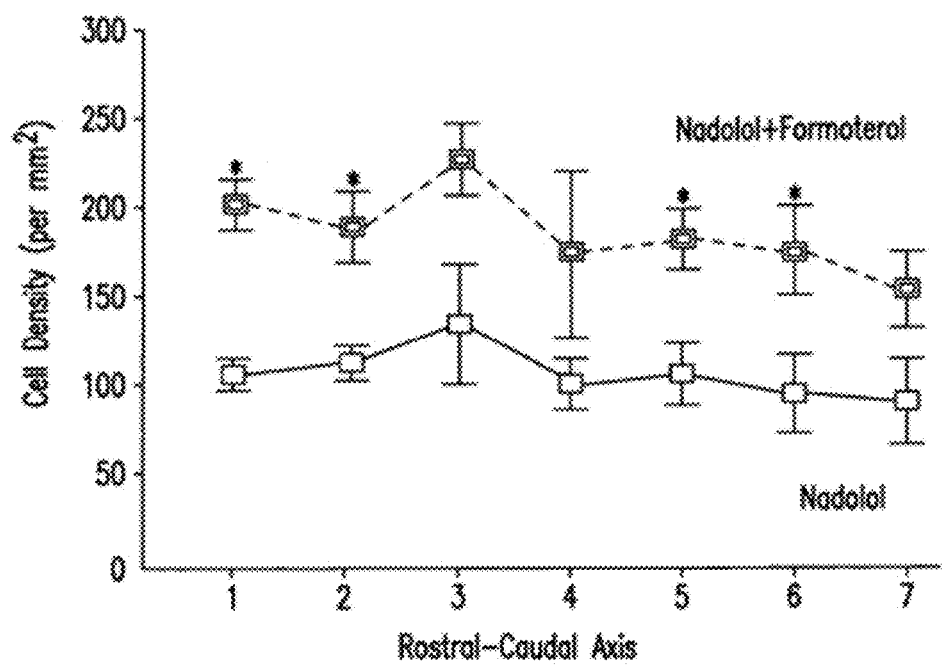
FIG. 6C

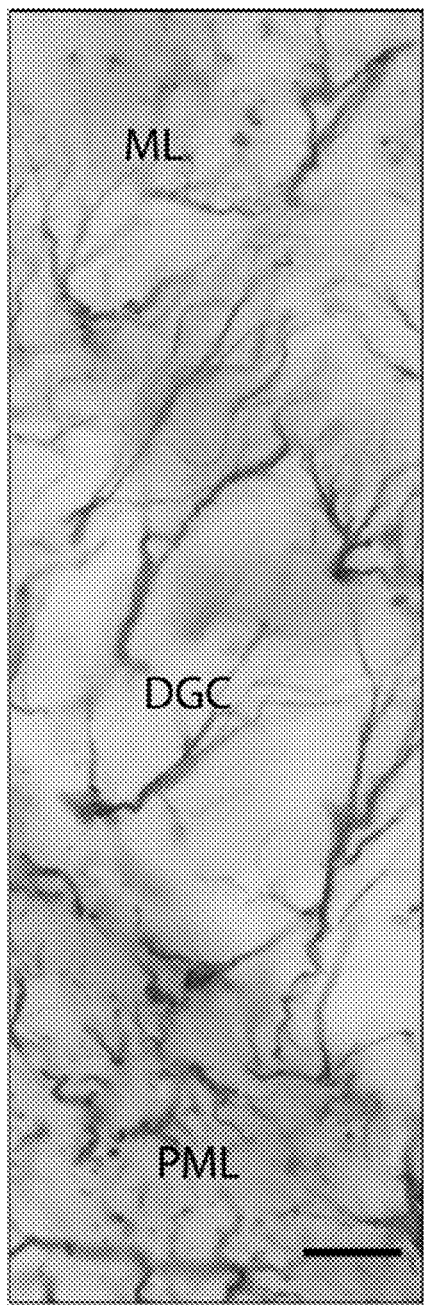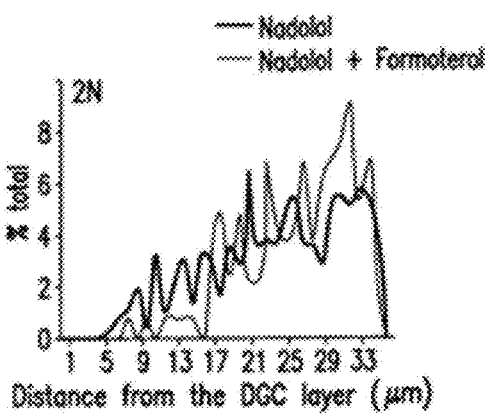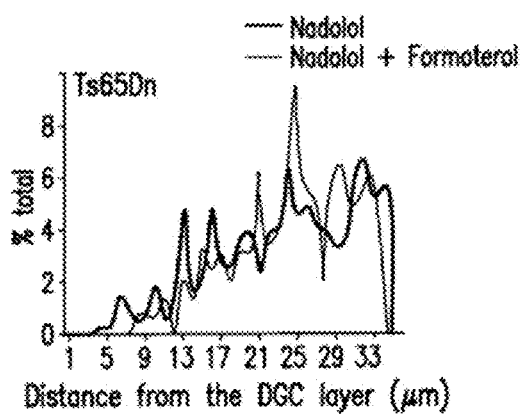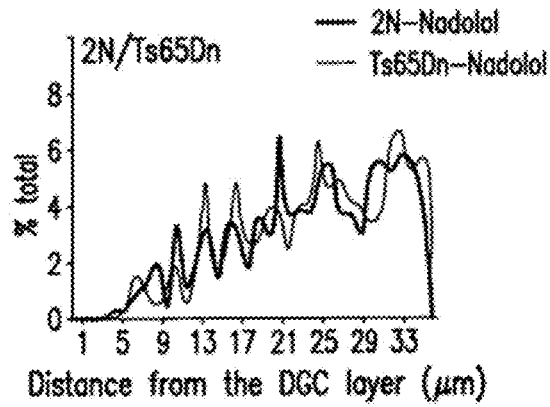
FIG. 7A
FIG. 7B
FIG. 7C
FIG. 7D

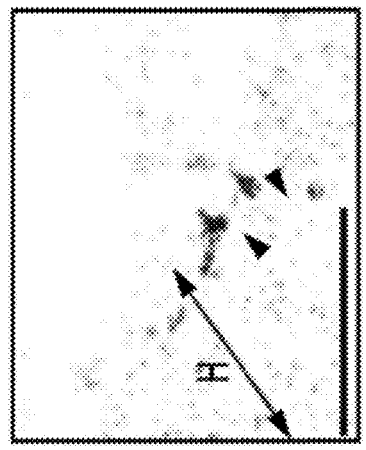
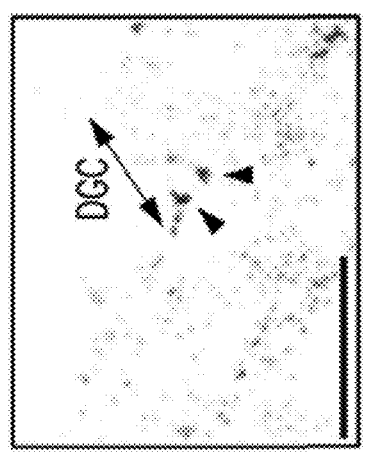
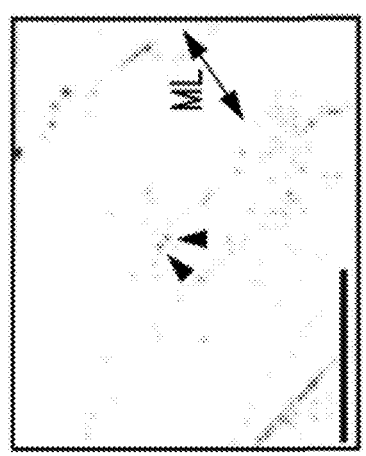
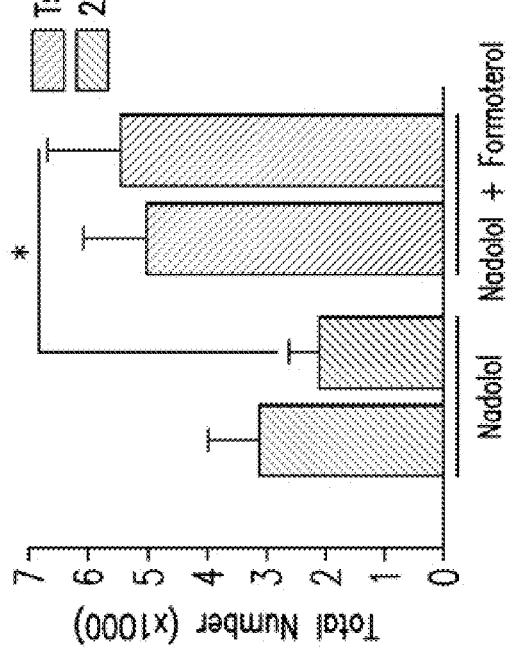
FIG. 8A
FIG. 8B
FIG. 8C
FIG. 8D
FIG. 8E

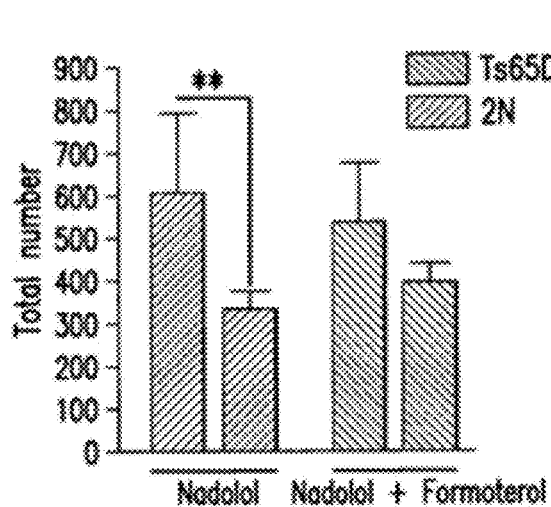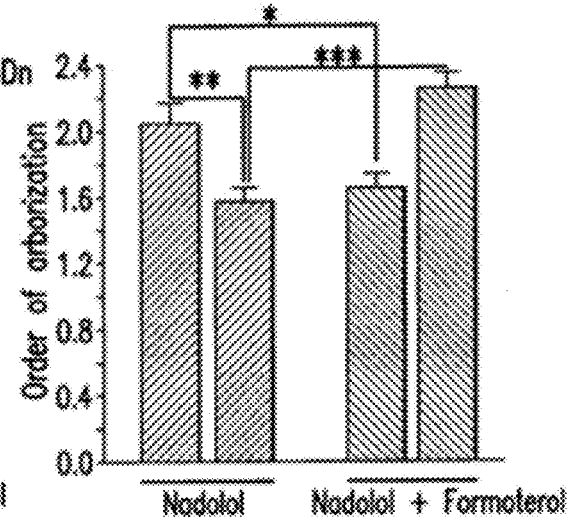
FIG. 8F  FIG. 8G
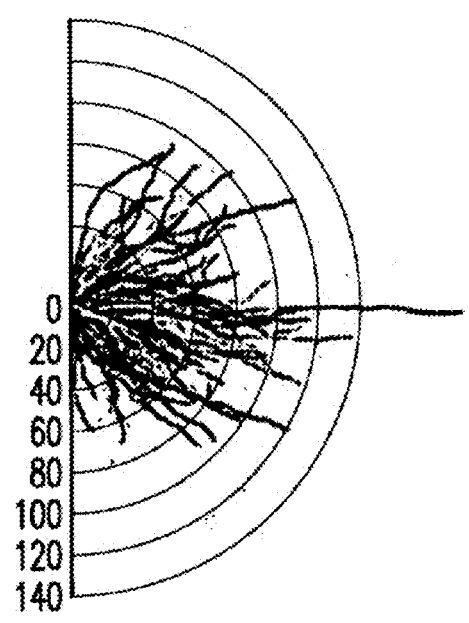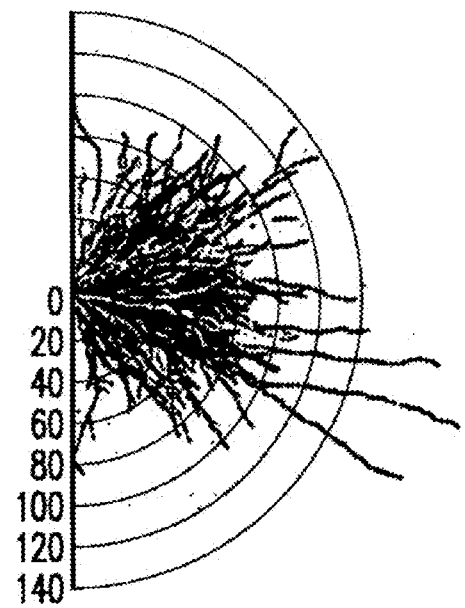
FIG. 8H

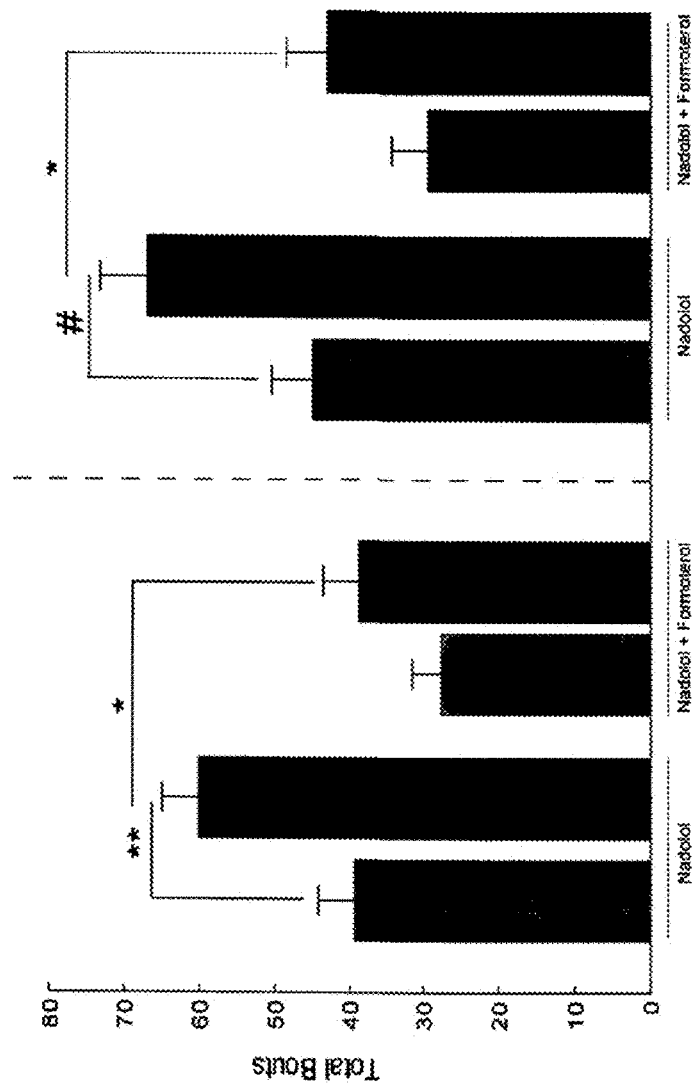
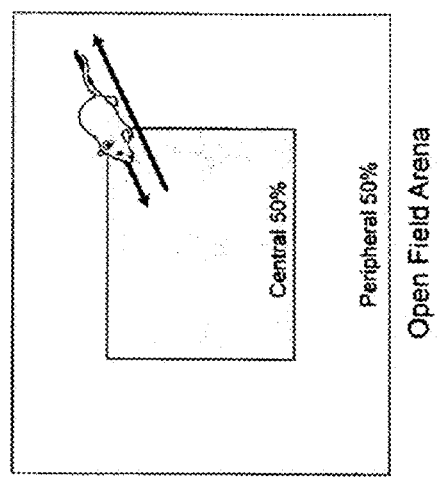
FIG. 11A
FIG. 11B
FIG. 11C

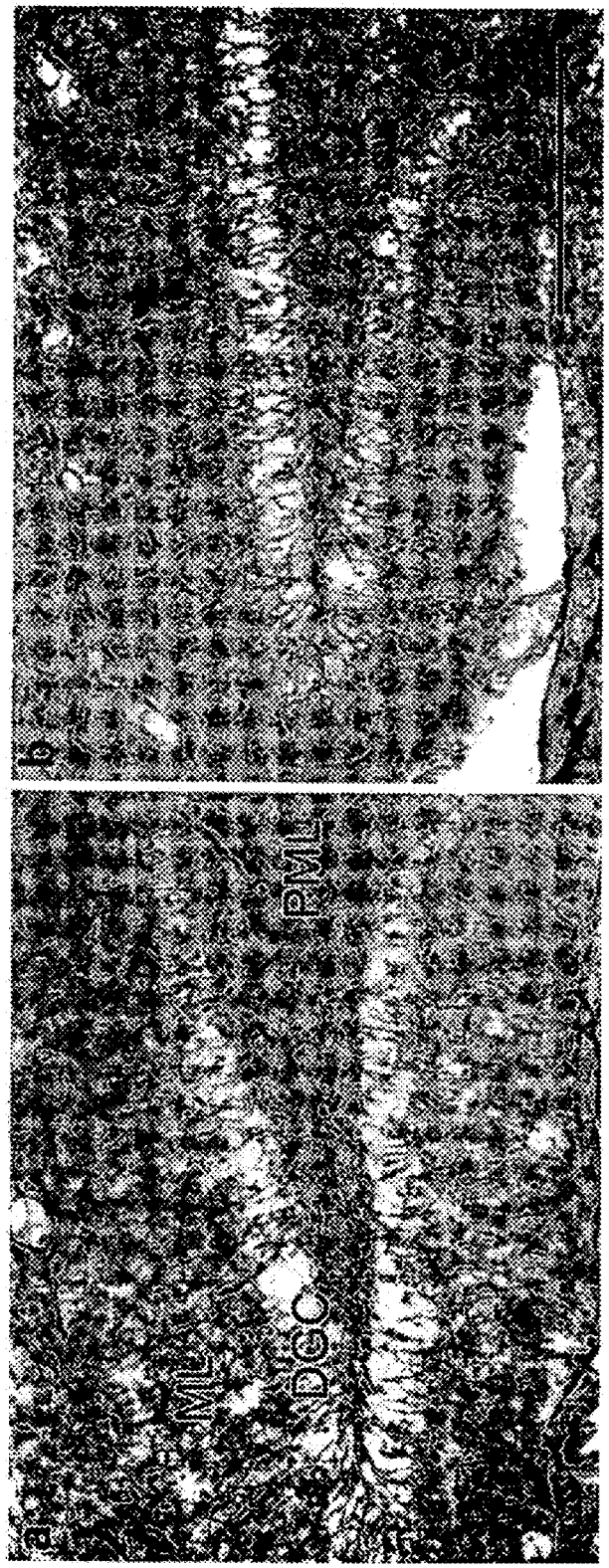

METHOD OF IMPROVING COGNITION AND INCREASING DENDRITIC COMPLEXITY IN HUMANS WITH DOWN SYNDROME AND COMPOSITIONS THEREFOR

The instant application, filed on 12 Feb. 2014, claims the benefit of U.S. Provisional Patent Application 61/850,309, filed on 13 Feb. 2013.

SEQUENCE LISTING

The instant application contains a Sequence Listing which has been submitted electronically in ASCII format and is hereby incorporated by reference in its entirety. Said ASCII copy, created on Mar. 18, 2014, is named 40702US_SL.txt and is 1,798 bytes in size.

BACKGROUND OF THE INVENTION

Worldwide, there are more than 5.8 million individuals with Down syndrome (DS). It is a complex multi-system disorder causing significant physical and psychological abnormalities throughout the lifespan of affected individuals. Nervous system dysfunction is the major cause of disability in individuals with DS. Co-morbidity between cognitive dysfunction and psychiatric conditions particularly, attention deficit hyperactivity disorder, further complicates the clinical symptomatology presented by DS. Later in adulthood, all individuals with DS develop brain pathology indistinguishable from that of Alzheimer's disease (AD). As a result, drastic improvement in the life expectancy of people with DS3 has been associated with a significant increase in the rate of dementia of AD type in these individuals. For this reason, there is an emerging need for developing effective therapeutic strategies for cognitive disabilities in children before the occurrence of AD pathology in their adulthood. By both increasing cognitive function in children with Down syndrome, and inhibiting or lessening adult onset AD brain pathology as these children reach adulthood, humans with Down syndrome will be capable of living longer, more productive lives.

SUMMARY OF THE INVENTION

The present invention provides a method of improving cognitive function and increasing dendritic complexity in humans exhibiting Down syndrome.

The present invention also provides pharmaceutical compositions for improving cognition and increasing dendritic complexity in humans exhibiting Down syndrome.

The present invention further provides a method for inhibiting onset of adult AD brain pathology in children with Down syndrome.

BRIEF DESCRIPTION OF THE DRAWINGS

FIGS. 1A-1G: FIG. 1A shows the total volume of hippocampus and its sub-regions were quantified in neuronal nuclei (NeuN)-stained brain sections from young adult (6 months) naïve mice; FIG. 1B) morphometric analysis showed no significant alterations in the hippocampus volume in Ts65Dn mice; FIGS. 1C-1D) show significant atrophy of the DGC layer and the molecular layer (ML) of the DG were detected in Ts65Dn mice compared to 2N controls; FIGS. 1E-1F) shows that atrophy of DGC and ML in Ts65Dn mice could be linked to alterations in the extent of the dendritic tree with a significant shortening of these dendrites in Ts65Dn mice; and FIG. 1G) shows that the most severe dendritic shortening in Ts65Dn mice occurred in the order 3.

FIG. 4A shows that in countering the peripheral effects of formoterol, nadolol, a βAR antagonist that does not cross the BBB, was used, and analysis of variance showed no significant effect of either genotype of treatment on oxygen saturation; and FIGS. 4B-4C) show that significant failure in contextual learning in young adult Ts65Dn mice was observed.

FIGS. 5A-5B show bar graphs of mean velocity and total distance traveled in the open field arena, respectively, for Ts65Dn mice. Treatment with formoterol led to a significant reduction in both velocity and total distance traveled in Ts65Dn mice, suggesting an improvement in their memory and attention; and FIGS. 5C-5D) show data plots of velocity and distance traveled versus minutes for both Ts65Dn mice and 2N mice.

FIG. 6A shows postmortem analysis of hippocampal samples indicated significant deficit in synaptic density in the DG in adult Ts65Dn mice compared with 2N mice. Treatment with formoterol led to a significant improvement in Ts65Dn mice, restoring synaptic density in DG in these mice; and FIGS. 6B-6C) show that treatment of Ts65Dn mice with formoterol restored the number of c-Fos-positive neurons to normal levels in the Ts65Dn mice.

FIG. 7A shows immunocytological visualization of GFAP-positive profiles from the DGC area with a significant increase of astrocytes being observed in Ts65Dn mice treated with formoterol. No significant effects of formoterol were found in the 2N group.

FIGS. 7B-7D depict frequency distribution of distances of GFAP-positive profiles from the DGC area. X-axes: distances from the DGC layer (um); Y-axes: % total. Mice: 2N (FIG. 7B); Ts65Dn (FIG. 7C); 2N/Ts65Dn (FIG. 7D).

FIGS. 8A-8C show BrdU-positive profiles (arrows) in the DG of a 2N mouse; FIG. 8D) shows that formoterol treatment caused a significant increase in the number of BrdU-positive profiles in Ts65Dn mice; FIG. 8E) shows the DCX-positive neurons in the DG of a 2N mouse; FIG. 8F) shows the number of DCX-positive DGCs in 2N and Ts65Dn mice; FIG. 8G) shows the order of branching in Ts65Dn and 2N mice; and FIG. 8H) shows the increase in the dendritic span in Ts65Dn mice treated with formoterol.

FIG. 11A illustrates that bouts are defined as the number of crossings from the peripheral area 50% area to the central 50% area and vice versa (open field arena); and FIGS. 11B-11C) illustrate a significant increase in the number of bouts from the central 50% area to the peripheral 50% area and vice versa in Ts65Dn mice. Formoterol treatment led to a significant reduction in the number of bouts in both central and peripheral 50% areas in Ts65Dn mice.

FIGS. 13A-13B shows immunocytological visualization of GFAP-positive astrocytes in the DG of a 2N (FIG. 13A) (leftside) and a Ts65Dn mouse (FIG. 13B)(right side). A drastic increase in the density of GFAP-positive profiles was found in the ML and the PML regions of the DG in Ts65Dn mice.

DETAILED DESCRIPTION OF THE PREFERRED EMBODIMENTS

Figure 1E:
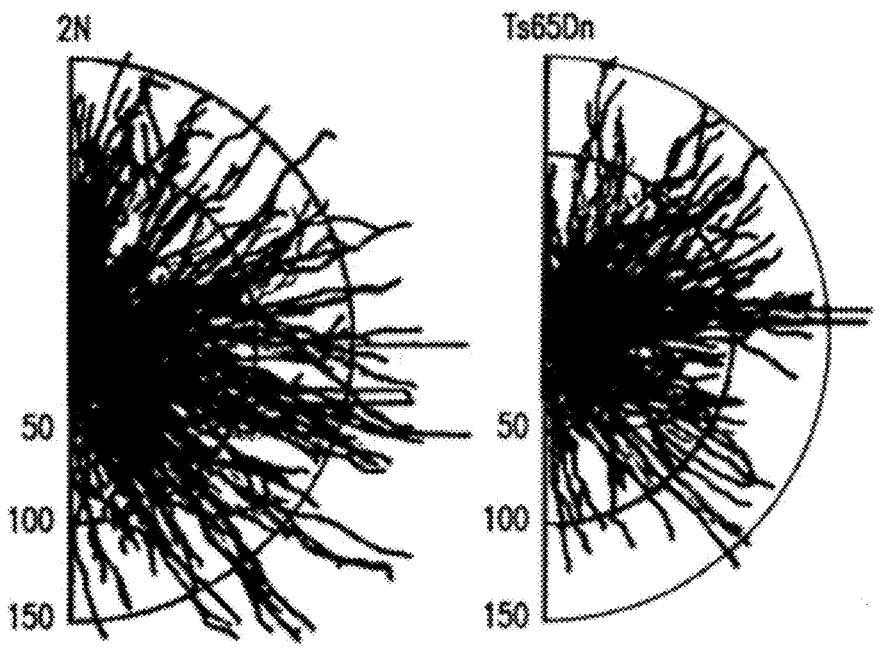

The present invention is based, in part, upon the discovery that β2 adrenergic agonists are advantageously used to improve cognition in humans exhibiting Down syndrome.

The present invention is also based, in part, upon the discovery that β2 adrenergic agonists are advantageously used to increase dendritic complexity in humans exhibiting Down syndrome.

The present invention is also further based, in part, upon the discovery that β2 adrenergic agonists are particularly advantageously used to improve cognition and increase dendritic complexity in humans with prior or co-administration of one or more β1 adrenergic antagonists.

The present invention is, moreover, based, in part, upon the discovery that onset of adult AD brain pathology in humans having Down syndrome can be inhibited by administering one or more β2 adrenergic receptors to a child having Down syndrome.

Term Definitions

As used herein, the term β2 agonist is used to mean β2-adrenergic receptor agonist or β2AR agonist. Moreover, the term β2 agonist is understood to include compounds that are primarily β2 agonists, but which may also be peripheral agonists for other adrenergic receptors as well, such as β1 adrenergic receptors.

β2 agonists that may be used in accordance with the present invention may be short-acting, long-acting or ultra long-acting. Examples of short-acting β2 agonists may be used are salbutamol, levosalbutamol, terbuline, pirbuterol, procaterol, metaproterenol, bitolterol mesylate, oritodrine, isoprenaline, salmefamol, fenoterol, terbutaline, albuterol, isoetharine, Examples of long-acting β2 agonists that may be used are salmeterol, bambuterol, formoterol and clenbuterol. Examples of ultra long-acting β2 agonists include indacaterol.

As used herein, the term β1 antagonist means β1 adrenergic receptor antagonist or simply β1-blocker. Examples of selective β1-blockers are nadolol, acebutolol, atenol, betaxolol, bisoprolol, celiprolol, esmolol, metaprolol and nebivolol.

The term "pharmaceutically-accepted salts" means acid addition salts that are commonly used in human or veterinary medicine and are deemed safe for use. Examples for the present invention include, but are not limited to, salts obtained from the following acids: acetic, ascorbic, benzenesulfonic, benzoic, camphosulfonic, citric, ethanesulfonic, edisylic, fumaric, gentisic, gluconic, glucoronic, glutamic, hippuric, hydrobromic, isethionic, lactic, nitric, phosphoric, succinic, sulfuric and tartaric; for example.

DS means Down syndrome.

AD means Alzheimer's Disease.

AD brain pathology refers to the accumulation of highly degradation-resistant amyloid fibers that cause lesions in areas of the brain proximate thereto. Accumulation of these amyloid fibers to neurotoxic levels leads to destruction of nerve fibers, which, in turn, leads to the observed behavior associated with Alzheimer's dementia. Observed behavioral symptoms, which become progressively more severe with progression of the disease, often include loss of vocabulary, incorrect word substitutions (paraphasias), loss of reading and writing skill, increased risk of falling, wandering, loss of speech, apathy and even loss of muscle mass.

Child, as used herein, means a human from about 5 to 20 years of age.

Adult, as used herein, means a human from about 21 years of age and older.

Test, as used herein, refers to a contextual learning test, and as applied to humans means specifically a spatial contextual leaning test or the ACTB, described below.

Increased dendritic complexity means an increased arbor complexity or an increased number of dendritic branch points at fixed intervals from neuronal cell bodies, such as in the dentate gyrus. The count of number of dendritic branch points at fixed intervals from neuronal cell bodies and any increase is known as a Sholl analysis.

Improving cognition means an improved score on a contextual learning test or the ACTB test as described hereinbelow.

The term "therapeutically effective amount" means an amount of a compound or composition as described hereinbelow effective or sufficient to improve cognition, increase dendritic complexity or inhibit onset of adult AD pathology. The term "frequency" as related thereto means the number of times a treatment is administered to a DS human in order to obtain the result of improved cognition, increased dendritic complexity or inhibition of adult AD pathology.

Generally, in accordance the present invention, one or more of the above selective β1-blockers are administered prior to or concurrently with one or more β2 agonists in order to inhibit or preclude agonism of β1 adrenergic receptors by the one or more β2 agomists. Although some β2 agonists are highly selective for β2 adrenergic receptors, such as formoterol, it is preferred to block β1 adrenergic receptors in accordance with the methods of the present invention in order to preclude, or at least minimize, any adverse peripheral cardiac effects on humans being treated. However, β2 agonists may be used by themselves without prior or concurrent administration of β1-blockers while still remaining within the scope of the present invention.

Figure 9:
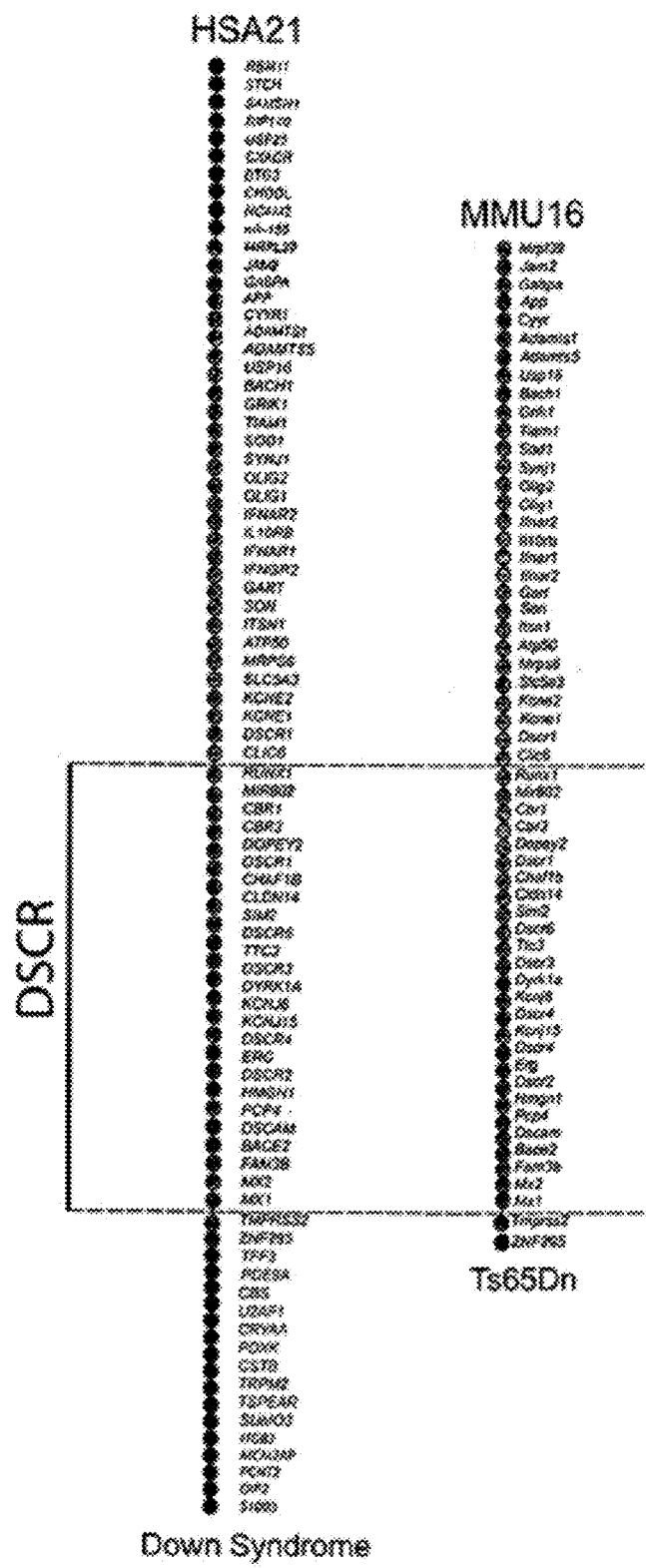
FIG. 9 illustrates a schematic representation of genes triplicated in DS and in the Ts65Dn mouse that play a role in nervous system abnormalities.

Creation of several transgenic mouse models has greatly facilitated progress it the understanding the neurobiological basis of cognitive dysfunction in DS. Among the mouse models, the Ts65Dn mouse is best characterized. It has an extra copy of approximately 140 mouse genes on chromosome 16, orthologous to those on human chromosome 21 (HSA21). Almost all genes in HSA21 with potential role in nervous system abnormalities are also found in Ts65Dn mice (FIG. 9). Similar to DS, alterations in the structure and function of the hippocampus and failure in the induction of long-term potentiation (LTP) have been extensively reported in Ts65Dn mice. Ts65Dn mice are widely used in DS research, and are considered to be an art-accepted model for investigations regarding DS in humans. Olson, L. E., et al, Dev. Dyn. 2004 July; 230(3):581-9.

DS is characterized by degeneration and dysfunction of multiple neuronal populations in the central nervous system (CNS). Among them, the hippocampal formation, i.e. the primary site for processing contextual learning shows significant abnormalities in DS. As a result, failure in contextual learning is a common finding in people with DS. To uncover the neurobiological basis of failed contextual learning in DS, we have carefully examined the integrity of subcortical regions extensively projecting to the hippocampal formation. Through extensive innervation, these subcortical regions impose strong modulatory influence on hippocampal neurons. Among these subcortical regions, LC is of particular importance. LC neurons in the brainstem are the sole supplier of massive norepinephrine (NE)-ergic terminals for the hippocampus and play a significant role in wakefulness, attention, and navigational memory. In our previous study, we found significant age-related degeneration of NE-ergic neurons of LC in Ts65Dn mice. Interestingly, the loss of LC terminals in Ts65Dn mice leads to further deterioration of cognitive dysfunction in these mice. Similarly, LC neurons undergo extensive age-dependent degeneration in DS. The critical role of NE-ergic system dysfunction in cognitive dysfunction in Ts65Dn has been supported by the fact that either increasing brain NE levels with L-threo-3,4-dihdroxyphenylserine (L-DOPS), i.e. a NE prodrug, or improving β adrenergic signaling using xamoterol, restored contextual learning in Ts65Dn mice. Although L-DOPS is in phase III clinical trial for the treatment of primary autonomic failure associated with Parkinson's disease, it is yet to be approved by the FDA and its long-term effects particularly in children have yet to be explored.

To identify an alternative and to expedite the process of drug development in DS, we tested the effects of adrenergic agonists on cognitive function that have already been approved for use in humans. NE binds to a family of G protein-coupled receptors including α (1 and 2) and β (1, 2, and 3) adrenergic receptors (AR). Through increasing cyclic adenosine monophosphate (cAMP) and activation of protein kinase A (PKA), β-adrenergic receptor (βAR) signaling plays a major role in memory retrieval and consolidation. The principle neuronal population of the dentate gyrus (DG), i.e. dentate granular cells (DGC), plays a major role in contextual learning predominantly express β2ARs. Accordingly, it has also been shown that while β2AR agonists can improve long-term memory and learning, blocking these receptors impairs memory consolidation in chicks. Moreover, the inhibition of LTP by amyloid β in the DG of rodent models of AD, has been found to be rescued by β2ARs agonists and not those acting on β1ARs.

Another reason in favor of the use of β2AR agonists in DS is their peripheral effects. In the periphery, a majority of β1ARs are found in the cardiovascular system. Since cardiac abnormalities are considered the most common cause of death in people with DS, one would need to avoid the long-term use of drugs targeting cardiovascular system in DS. Considering the effectiveness and safety of the various types of βAR agonists, targeting β2ARs might be superior to those acting on β1ARs for improving contextual learning in DS.

For almost half a century, β2ARs have been attractive targets for pharmacological interventions in respiratory disorders. Accordingly, numerous long-acting β adrenergic drugs have been developed and widely prescribed in humans. Formoterol (Foradil™) is a long-acting β2AR agonist that shows 300 times more selectively for β2ARs than β1ARs. This drug is currently prescribed for relieving respiratory symptoms associated with asthma, exercise-induced bronchospasms, and chronic obstructive pulmonary disease. The lipophilic nature of formoterol allows it to be easily deposited into the cell membrane facilitating its long-term action on adrenergic receptors. The drug has been shown to cross the blood brain barrier (BBB) and reach the brain in rats and dogs. For instance, it has been shown that intraperitoneal (IP) injections of formoterol in rodents led to a significant increase in expression of interleukins particularly IL-10 in the hippocampus.

As we describe herein, for example, the use of formoterol in adult Ts65Dn mice was safe and led to a significant improvement in contextual learning and restoration of synaptic density in the DG Ts65Dn mice. Furthermore, fomoterol treatment was linked to a significant increase in the rate of cell proliferation and dendritic complexity of newly born neurons in the DG. This result clearly evidences that the use of β2ARs as described hereinbelow are effective in improving cognition in humans with DS.

In order to further illustrate the present invention, reference will now be made to certain examples which are provided solely for purposes of illustration and are not intended to be limitative.

Examples

Figure 1F:
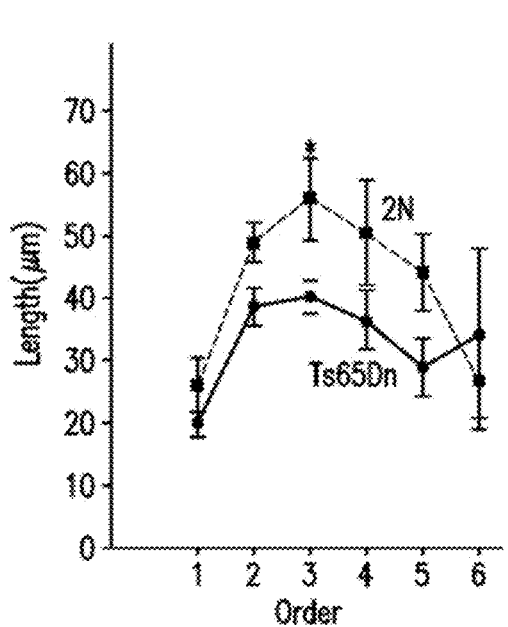

The total volume of hippocampus and its sub-regions were quantified in neuronal nuclei (NeuN)-stained brain sections from young adult (6 months) naive mice (FIG. 1A). Although morphometric analyses showed no significant alterations in the hippocampal volume in Ts65Dn mice (FIG. 1B), a significant atrophy of the DGC layer (P=0.032) and the molecular layer (ML) of the DG (P=0.0267) were detected in Ts65Dn mice compared to 2N controls (FIGS. 1C-1D). ML primarily consists of DGC dendrites. To test whether atrophy of DGC and ML in Ts65Dn mice could be linked to alterations in the extent of the dendritic tree, we studied the DGCs' dendrites in adult Ts65Dn mice and their age-matched controls and found a significant shortening of these dendrites in Ts65Dn mice (P=0.016, FIGS. 1E-1F).

Figure 1G:
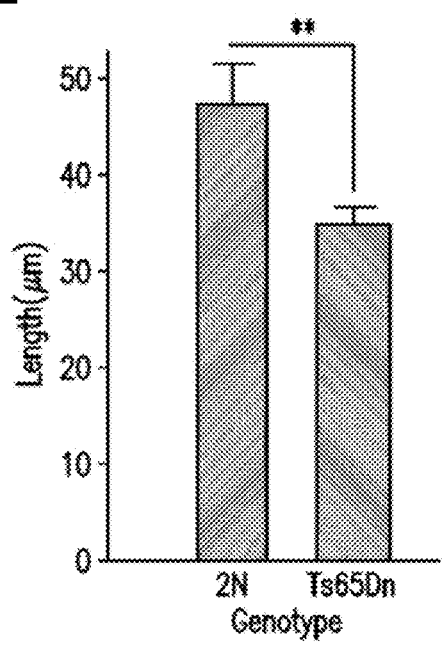

Interestingly, the analysis of the relationship between dendritic lengths and the order of arborization showed that the most severe shortening of dendrites in Ts65Dn mice occurred in the order 3 (FIG. 1G).

Figure 2A:
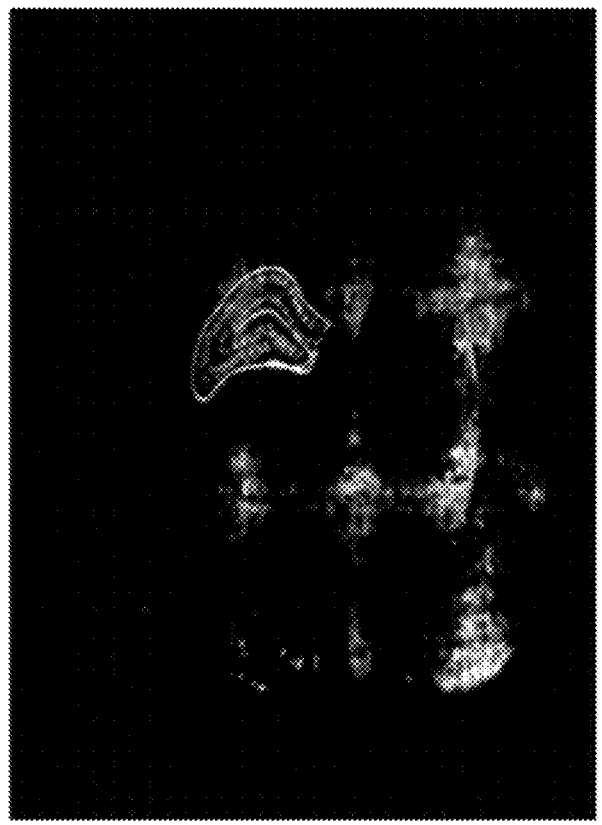
FIGS. 2A-2B show significant reduction in cAMP levels in micro-punches through the DG in adult Ts65Dn mice as detected by enzyme-linked immunoabsorbent assay (ELISA), suggesting failed AR signaling in the hippocampus in untreated Ts65Dn mice.
Figure 2B:
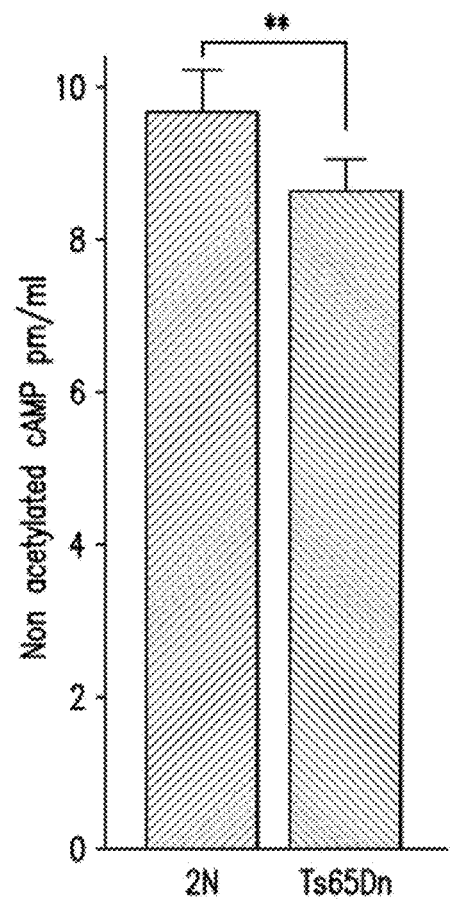

The hippocampal region receives extensive innervation from LC neurons[23]. As we have reported before, LC neurons undergo significant age-dependent degeneration in the Ts65Dn mouse leading to reduced levels of available NE in the hippocampus[12]. Binding NE to ARs leads to the formation of the secondary messenger cAMP, a critical mediator of cell signaling. We asked whether reduced NE levels in the hippocampus in naive Ts65 Dn could be linked to alterations in cAMP levels in these mice. Using enzyme linked immunosorbent assay (ELISA), we found significant (P=0.002) reduction in cAMP levels in micro-punches through the DG in adult Ts65Dn mice, suggesting failed AR signing in the hippocampus to untreated Ts65Dn mice (FIGS. 2A-2B).

Figure 3C:
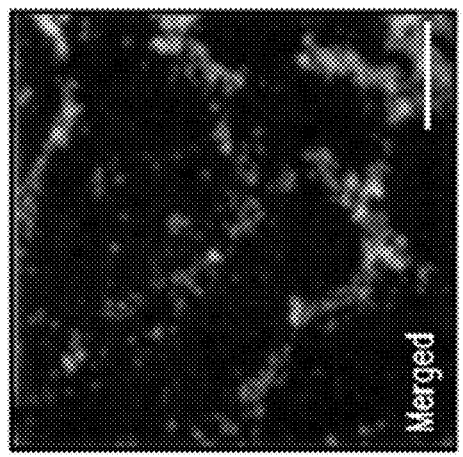
FIGS. 3A-3C show that a majority of β2ARs were co-localized with a major synaptic vesicle Protein, the synaptophysin, FIGS. 3D-3G) show that frequency distribution of the area covered by β2ARs staining within the DGC layer.
Figure 3F:
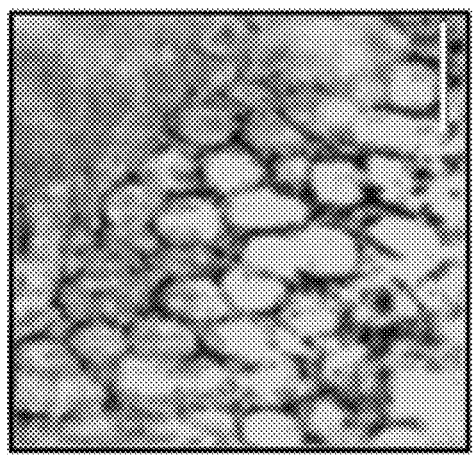
FIG. 3H) shows a significant shift to higher values in adult Ts65Dn mice compared with 2N mice.
Figure 3B:
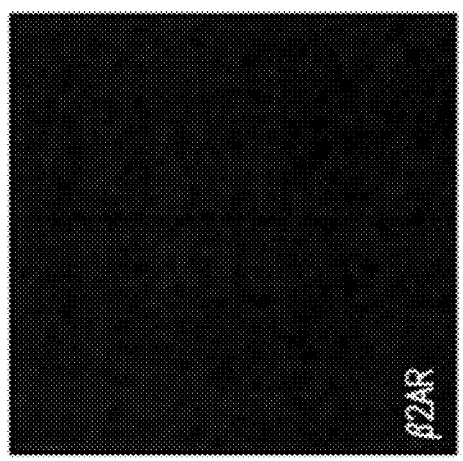
Figure 3E:
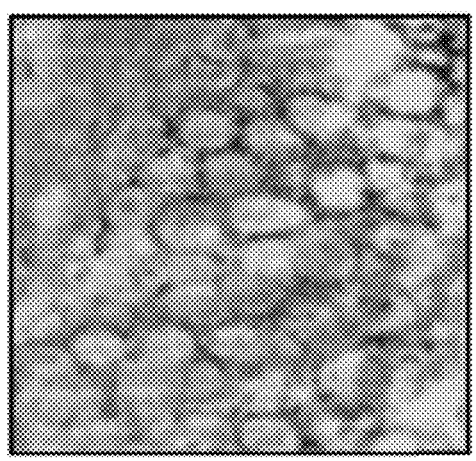
Figure 3A:
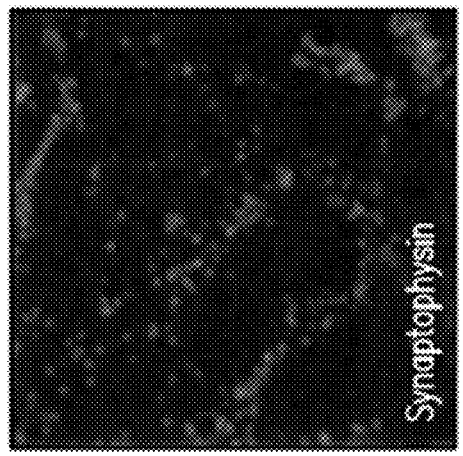
Figure 3D:
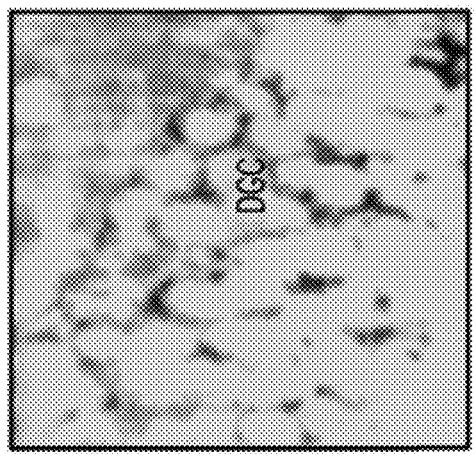

To study the status of β2ARs within the hippocampus, we stained brain sections of adult Ts65Dn mice (5-6 months) and their 2N controls with a polyclonal antibody against β2ARs. Unlike β1ARs that were predominantly found in the polymorphic layer of the DG[12], β2ARs were detected abundantly on the cell membrane of DGCs (FIGS. 3A-3C). Furthermore, a majority of β2ARs were co-localized with a major synaptic vesicle protein, i.e. synaptophysin, in DGCs. Frequency distribution of the area covered by β2ARs staining within the DGC layer (FIGS. 3D-3G) showed a significant (P<0.001, $X^2$=91.343) shift to the higher values in adult Ts65Dn (FIG. 3H) compared with 2N mice. Furthermore, the analysis of β2ARs in hippocampal synaptosomes showed a trend toward increased levels of β2ARs in the synaptosomes in Ts65Dn mice (2N=102.144±13.85; Ts65Dn=115.680±13.59, P=0.206), suggesting that β2AR remains intact in Ts65Dn mice in spite of significant LC degeneration.

The lack of significant decrease in β2ARs in Ts65Dn mice encouraged us to test the effects of a β2AR agonist, i.e. formoterol on cognitive function in these mice. Since β2ARs are mainly found on the smooth muscle cells in the respiratory system, we started by investigating the effects of formoterol on the respiratory as well as cardiovascular systems.

Figures 10A, 10B:
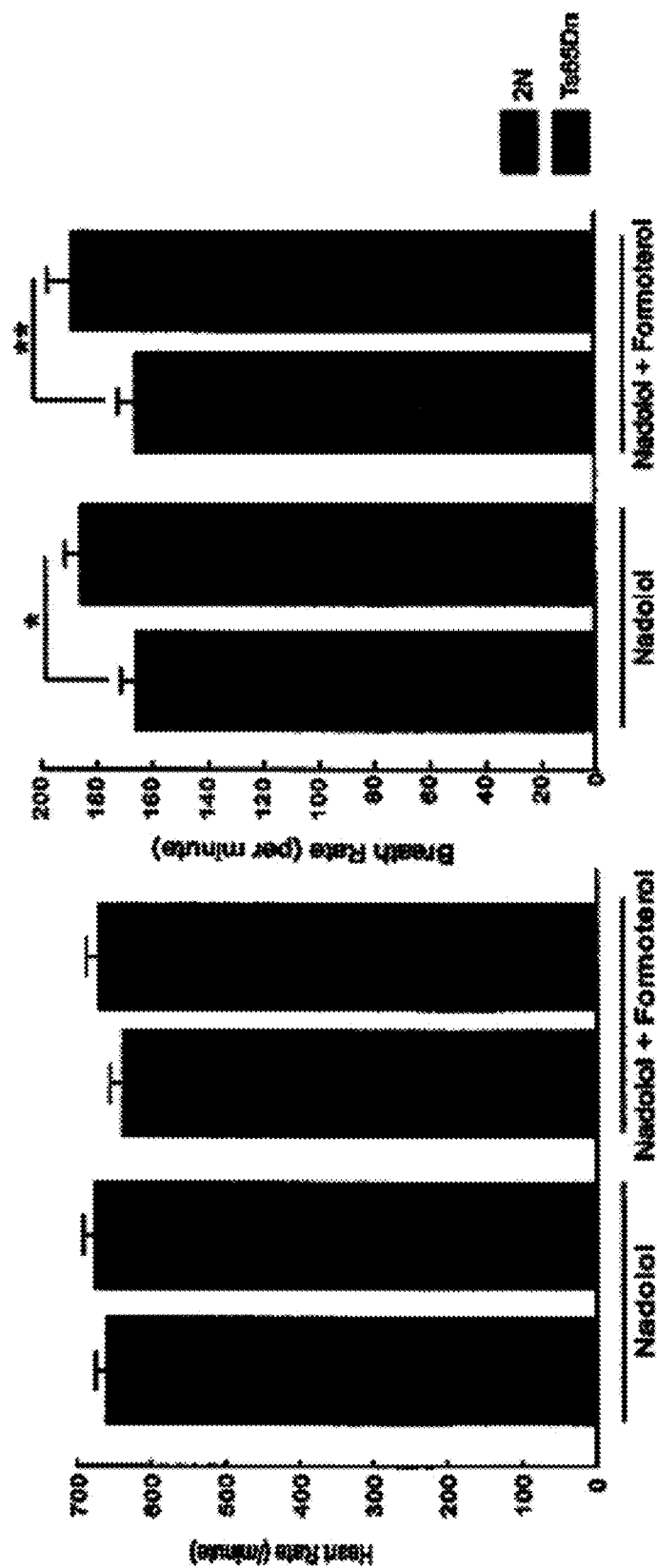
FIG. 10A shows that no significant effects of formoterol were found on heart rate.
FIG. 10B) shows that no significant effects of formoterol were found on the respiratory rate.

To counter the peripheral effects of formoterol, we used nadolol, i.e. a βAR antagonist that does not cross the BBB. Analysis of variance (ANOVA) showed no significant effects of either genotype or treatment on oxygen saturation (FIG. 4A, genotype: P=0.120, F=2.595; treatment: P=0.259, F=1.335) or the heart rate (FIG. 10A, genotype: P=0.104, F=2.852; treatment: P=0.369, F=0.839). However, we found a significantly higher respiratory rate in Ts65Dn compared with 2N controls (FIG. 10B, genotype: P=0.002, F=11.82; treatment: P=0.770, F=0.09). Accordingly, Fisher's post-hoc analysis showed significantly higher respiratory rate (11%) in Ts65Dn compared with 2N mice (P=0.028).

No peripheral effects of formoterol treatment in Ts65Dn and 2N mice encouraged us to proceed with testing the effects of formoterol treatment on cognition in Ts65Dn mice. Similar to our previous study, we found significant failure in contextual learning in young adult (6 months) TS65Dn mice (FIGS. 4B-4C). Interestingly, treating Ts65Dn mice with formoterol led to a significant improvement in their contextual learning (P<0.0001, FIG. 4B). Quantifying the rate of freezing within the first five minutes of exposure to the context in which they were initially shocked, Ts65Dn mice treated with formoterol showed a significant increase in freezing behavior compared with the Ts65Dn mice treated with only nadolol (P<0.0001, FIG. 4C).

Open field activity has been shown to be a reliable tool for assessing cognitive function in Ts65Dn mice. Ts65Dn mice showed significantly higher velocity and total distance travelled as compared to 2N in the open field arena (FIGS. 5A-5D). Interestingly, treatment with formoterol led to a significant reduction in both velocity (P=0.0014, FIG. 5A) and total distance travelled (P=0.001, FIG. 5B) in Ts65Dn mice, suggesting an improvement in their memory and attention.

To further analyze alterations in the pattern of activity, the location of each mouse in the open field arena was automatically determined. The total number of entries (bouts) from peripheral 50% area of the arena to the central 50% area and vice versa was quantified. We found significantly higher number of bouts in Ts65Dn mice as compared to their 2N controls (P=0.002 for central area; P=0.007 for peripheral area). Interestingly, the use of formoterol led to a significant reduction in the number of bouts in Ts65Dn mice (P=0.011 for central area; P=0.017 for peripheral area) (FIGS. 11A-11C).

To test whether improving β2AR signaling by formoterol would alter hippocampal synaptic strength; we studied presynaptic vesicles in this region. Using an antibody against synaptophysin, we found a significant reduction in the synaptic density in the DG of the hippocampus in Ts65Dn compared with 2N mice (P=0.008). Interestingly, treatment with formoterol led to a significant increase in synaptophysin immunoreactivity in the DG of Ts65Dn mice (P=0.035, FIG. 6A).

To test whether increased β2AR signaling would also improve neuronal activity in DGCs, we studied the expression of c-Fos in these cells. Using an antibody against c-Fos, the numerical density of c-Fos positive-cells in the DGC layer was studied (FIGS. 12A-12D). While we found a significant reduction in the number of c-Fos-positive profiles in Ts65Dn mice compared with 2N mice (P=0.0072), treatment with formoterol restored the number of c-Fos positive cells in Ts65Dn mice to that of controls (2N) (P=0.00014, FIGS. 6B-6C).

In addition to neurons, astrocytes express both β1AR and β2ARs. Indeed, βAR signaling promotes cAMP production in astrocytes. We questioned whether improving β2AR signaling would also influence the status of astrocytes in the hippocampus. Using an antibody against glial fibrillary acidic protein (GFAP), sections throughout the septo-temporal extent of the hippocampus were stained. A large number of astrocytes were labeled throughout the DG. Indeed, most DGCs in the hippocampus were surrounded by numerous astrocytes (FIG. 7A). Interestingly, while we found a significant increase in the density of GFAP-positive profiles in the DG of Ts65Dn mice (P=0.045; FIGS. 5A-5D), no effects of formoterol treatment were detected on either the density of GFAP-positive cell bodies or their processes. Studying the position of GFAP-positive profiles in relationship to the ML, we found that formoterol treatment was associated with a significant increase in the distance between the GFAP-immunoreactive profiles and the DGC layer in Ts65Dn mice (P=0.032, FIGS. 7B-7D, 14).

It has been shown that NE can increase the rate of neurogenesis in the hippocampus of rodents. Interestingly, Matsuda and colleagues recently reported that, β2ARs and not β1ARs mediate this effect. We studied whether improving β2 signaling with formoterol could also alter the rate of cell proliferation and neurogenesis in Ts65Dn mice. To achieve this, we used 5-bromo-2-deoxyuridine (BrdU), i.e. a synthetic nucleotide that can be incorporated into the newly synthesized DNA of replicating cells. Both 2N and TS65Dn mice were treated with either nadolol alone or a combination of nadolol and formoterol, followed by BrdU treatment. We found a significant number of BrdU-positive profiles in the sub-granular region of the DG in both Ts65Dn and 2N mice (FIG. 8A). Stereological counting of the total number of BrdU-positive profiles revealed 37% reduction in the DGC layer Ts65Dn mice compared to 2N mice (FIG. 8A). Interestingly, the treatment with formoterol led to around 1.5-folds increase in Ts65Dn mice (P=0.031, FIG. 8B) and 0.6 folds increase in 2N mice (P=0.191), in the number of BrdU-positive profiles. ANOVA showed significant effects of treatment (P=0.018, F=6.749) and no effects of genotype (P=0.762, F=0.094) on the number of BrdU-positive profiles in the mice treated with BrdU.

To test whether formoterol treatment would indeed influence neungenesis, we investigated the effects of formoterol on doublecortin (DCX)-positive DGCs and the extent of their dendrites. We found that a significant number of DGCs and their dendrites were labeled (FIG. 8E). Although we found a significant reduction in the number of DCX-positive neurons in Ts65Dn mice, formoterol treatment had no significant effects on the total number of DCX-positive neurons (FIG. 8F). However, we found that formoterol treatment was associated with a significant increase in the complexity of dendritic tree in DCX-positive neurons in Ts65Dn mice (P=0.000075, FIG. 8G). Interestingly, formoterol treatment also led to a significant decrease in the order of dendritic arborization in 2N mice. (P=0.018, FIG. 8H).

In order to identify mechanisms by which β2AR signaling promotes cell proliferation, we studied the expression levels of genes believed to induce neurogenesis in the hippocampus. FGF2 has been shown to play a key role in proliferation and differentiation of adult neuronal progenitors. Our real-time PCR experiments showed around 70% reduction in Fgf2 mRNA levels in micro-punches through the DG of Ts65Dn mice compared to 2N counterparts (FIG. 15; P=0.015, F=6.099). Although formoterol treatment led to increased gene expression for Fgf2 in both Ts65Dn (20%) and 2N (80%) mice, the increase was only significant in 2N mice (P=0.044, t=2.084).

DS is characterized by significant degeneration of NE-ergic neurons of LC. These changes have been recapitulated in the Ts65Dn mouse model of DS. LC neurons in the brainstem, project extensively to hippocampal and cortical regions. It has been shown that, in rodents, individual LC neurons can project to both hemispheres or both hippocampal and cerebellar regions within the same hemisphere. Extensive innervation of the hippocampus enables LC neurons to exert a strong modulatory influence on incoming sensory and navigational information to this region. For this reason, it is not surprising that degeneration of LC neurons in DS would lead to significant structural and behavioral abnormalities in the hippocampus of affected individuals.

Although the molecular mechanisms behind the loss of LC neurons in DS have yet to be fully elucidated, studying the role of individual triplicated genes in DS might shed some light on this issue (FIG. 9). Among more than 100 triplicated genes in DS, App overexpression has been found to play a major role in LC degeneration in both DS and the Ts65Dn mouse model. Our previous studies have unequivocally linked App overexpression to failed axonal transport in cholinergic neurons in Ts65Dn mice. It is tempting to suggest that, through a similar mechanism; failed axonal transport in LC neurons plays a role in their selective vulnerability in DS. We are currently testing this hypothesis.

LC neurons are significantly affected by neurofibrillary degeneration in both DS and AD. Indeed, a recent study by Braak and colleagues found that healthy individuals develop signs of neurofibrillary degeneration in LC neurons as early as 6 years of age. Interestingly, LC degeneration seems to precede the degeneration of other brain regions commonly involved in DS and AD. Our previous investigations revealed significant degeneration of both cholinergic neurons of basal forebrain and NE-ergic neurons of LC in Ts65Dn mice. Since both nueronal populations provide extensive innervation to the hippocampus, we suggested that degeneration of these neurons would lead to "de-afferentation" of the hippocampal region in Ts65Dn mice.

In the present study, we found significant atrophy of the ML and DGC areas of the DG in adult Ts65Dn mice (FIGS. 1A-1G). Major constituents of the DGC area and the ML are DGC's cell body and their dendrites respectively. We found a significant atrophy of DGCs and shortening of their dendrites in Ts65Dn mice (FIG. 1B). Interestingly, the most severe shortening occurred in the $4^{th}$ order of branching in DGC dendrites, i.e. an area corresponding to a region of ML with the highest density of β2ARs in rodents.

Significant age-depended degeneration of LC neurons, reduced density of NE-ergic terminals, diminished NE levels in the hippocampus, and failed contextual learning in Ts65Dn mice all support failure of NE-ergic system in Ts65Dn mice. In the present study, we also found evidence on failed adrenergic receptors signaling in Ts65Dn mice as suggested by diminished cAMP levels in the hippocampus (FIGS. 2A-2B). Interestingly, increasing brain NE levels using L-DOPS, i.e. a prodrug for NE, could successfully restore cognitive function in Ts65Dn mice in spite of significant LC degeneration. Since L-DOPS is yet to be approved for use in the US, the use of alternative drugs already approved, particularly in children, would be an attractive strategy.

The use of formoterol enabled us to test the effects of improving β2AR signaling on cognitive function in mice with significant degeneration of LC neurons. Although formoterol binds to all three human βARs, it shows 300-fold more affinity for β2ARs than β1ARs. This suggests that observed effects of formoterol in this study were predominantly mediated via β2ARs. Upregulation of β2ARs in the DG in Ts65Dn mice (FIGS. 3A-3H) suggests that, in spite of significant LC degeneration in these mice, βAR signaling is still intact.

Formoterol has been shown to reach the brain within 30 minutes of oral administration in rodents. Sasaki and colleagues found that, 3 hours after oral administration of formoterol in rats, the drug concentration in the brain was around 30% of that of plasma. Interestingly, the drugs levels in the brain were more stable as compared to that of plasma or lungs. IP injections of formoterol in rodents also led to a significant increase in gene expression for interleukin (IL)-1β and IL-1 receptor-II in cortical and hippocampal samples. Importantly, by using β blockers with and without the ability to cross the BBB, the authors showed that the induction of IL gene expression after formoterol treatment was indeed central.

As we report here, we found that formoterol treatment led to a significant improvement in contextual learning (FIGS. 4B-4C) and reduced the severity of hyperactivity (FIGS. 5A-5D) in Ts65Dn mice. In the clinic, formoterol is primarily used for short-term treatment of asthma in humans and leads to significant improvement in respiratory functions. For this reason, we questioned whether the positive cognitive effects of formoterol in Ts65Dn mice were due to its beneficial peripheral effects on the respiratory system. As shown in FIG. 5A, we found no significant effects of formoterol on oxygen saturation in either 2N or Ts65Dn mice (FIG. 4A). This suggests that the observed improvements in cognitive functions in Ts65Dn mice were not due to increased supply of oxygen to the brain.

Our present data indicate that in addition to Ts65Dn mice, treatment with fomoterol led to improvement in contextual learning in 2N mice (FIGS. 4B-4C). The positive effects of adrenergic drugs in 2N mice have been shown before. As we reported before, xamoterol, i.e. a primarily β1AR agonist, can significantly improve contextual learning in Ts65Dn mice.

However, later studies showed that this drug did not improve spatial learning and/or reduce hyperactivity in Ts65Dn mice. The fact that unlike xamoterol, formoterol was able to reduce hyperactivity in Ts65Dn mice (FIGS. 5A-5D) suggests that various aspects of cognition are modulated by different types of βARs. Since formoterol was able to both improve contextual learning and reduce hyperactivity in Ts65Dn mice, it would suggest that β2AR agonists with the ability to cross the BBB would be attractive therapeutic agents in DS.

Postmortem analysis of the hippocampal samples showed significant deficit in synaptic density in the DG in adult Ts65Dn mice (5-6 months) compared with 2N mice (FIG.

6A). Interestingly, treatment with formoterol led to a significant improvement in Ts65Dn mice restoring synaptic density in DG in these mice. This is in accordance with the observed positive effects of NE and βAR agonists on the induction of LTP in the DG in rodents.

c-Fos is an immediate early gene that codes for a 55-kDa nuclear transcription factor, leading to a significant increase in gene expression. It has been shown that treatment with β adrenergic drugs leads to significant increase in c-Fos expression in rodents. To test whether increased β2AR signaling led to elevated c-Fos levels in the DG, we studied the levels of c-Fos in DGCs in formoterol-treated animals. While we found a significant reduction in the number of c-Fos-positive profiles in the DGC layer in Ts65Dn mice compared with 2N mice, treatment with formoterol restored the number of c-Fos-positive neurons to normal levels in the Ts65Dn mice (FIGS. 6B-6C). This suggests that formoterol treatment can lead to a significant increase in neuronal activity and gene expression in DGCs in Ts65Dn mice.

Failure in adult neurogenesis has been suggested to play a significant role in cognitive dysfunction in DS. Contestabile and colleagues found a significant reduction in cell proliferation in the DG of the dorsal hippocampus in DS fetuses and Ts65Dn mice. Furthermore, both environmental enrichment and a serotonin re-uptake inhibitor i.e. fluoxetine, have shown to promote neurogenesis in Ts65Dn mice. Using BrdU staining, we found 40% reduction in the cell proliferation in the DG in TS65Dn mice compared with 2N mice. Interestingly, we found that treatment with formoterol led to a significant improvement in cell proliferation in both groups, particularly in Ts65Dn mice (FIGS. 8A-8D). To investigate the fate of the newly born cells in the DG, we used DCX, a microtubule associated protein, as a marker for cells destined to become neurons. While we found a very significant decrease in the number of DCX-positive cells with dendrites in Ts65Dn mice, no effects of formoterol were detected on the total number of DC-positive cells in either genotype. Interestingly, formoterol treatment led to a significant increase in the complexity of dendrites of DCX-positive cells in Ts65Dn mice as shown by the order of dendritic branching (FIGS. 8E-8H). Surprisingly, we also found that formoterol treatment led to a significant reduction in the dendritic complexity in 2N mice (FIGS. 8E-8H). This could suggest that although formoterol treatment can lead to significant improvement in contextual learning in both Ts65Dn and 2N mice, it would induce desirable structural alterations only in the context of abnormal circuits found in Ts65Dn mice.

Figure 14:
FIG. 14 shows the distance between an arbitrary line drawn in the middle of the DGC layer and the position of GFAP-positive profiles (arrows depict the distance between the DGC layer and individual astrocytes.

Ts65Dn mice show a significant increase in the number of astrocytes in DG. βAR activation seems to improve the ability of astrocytes to increase $K^+$ clearance during neuronal activity. To test whether formoterol could also alter astrocytes, we studied GFAP-positive profiles in the DG. In accordance to previous studies, we found a significant increase in the number of GFAP-positive profiles in the DG of Ts65Dn mice compared with 2N controls. However, we did not detect any effects of formoterol on the number of astrocytes (FIGS. 13A-13B) in either 2N or Ts65Dn mice. Interestingly, we found that formoterol treatment led to a significant increase in the distance between GFAP-positive profiles in the ML and DGC layer in both 2N and Ts65Dn mice (FIG. 14).

Figure 15:
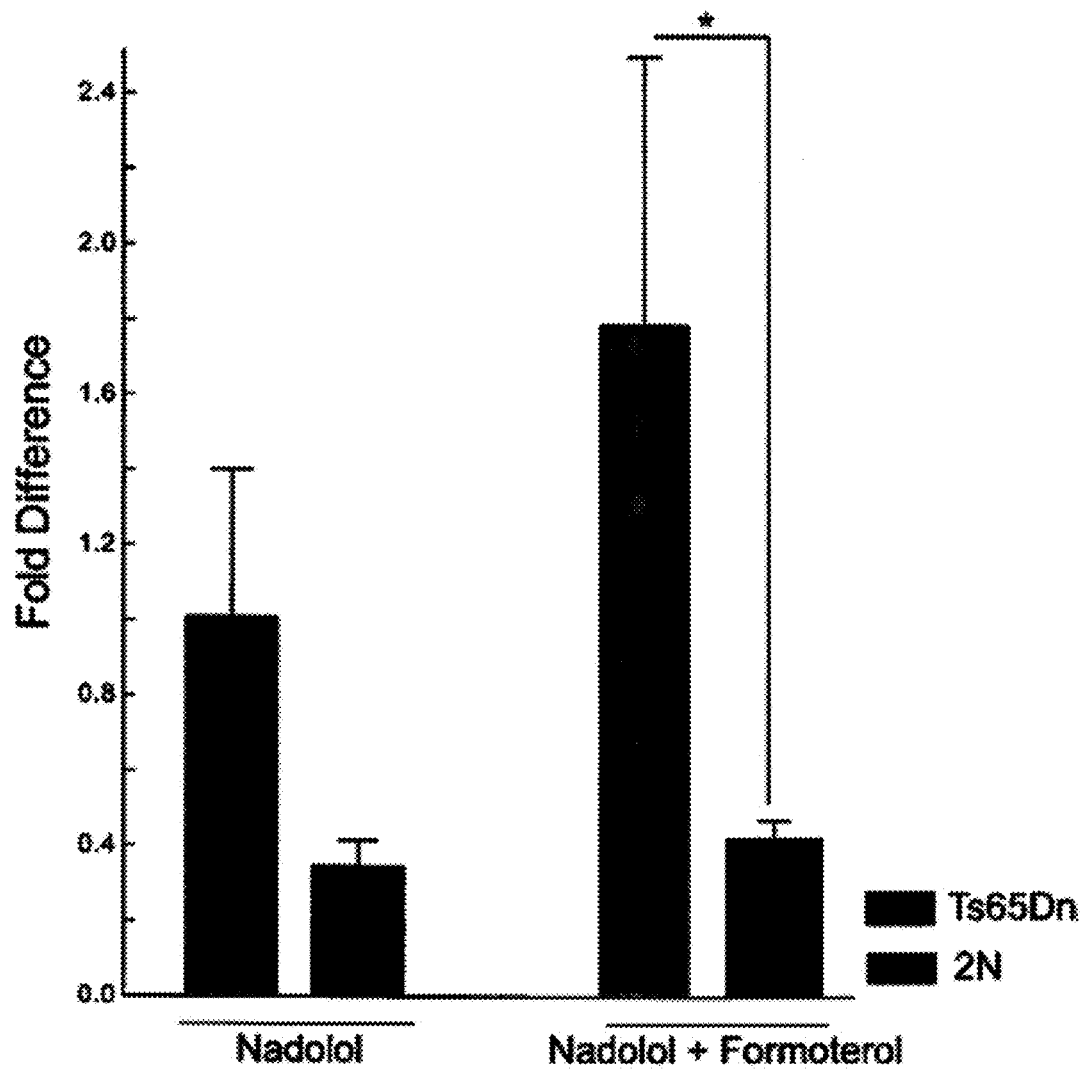
FIG. 15 illustrates a significant increase in gene expression for Fgf2 in micro-punches through the DG of Ts65Dn mice.

The mechanism by which β2AR signaling might improve neurogenesis in the DG in Ts65Dn mice remains to be fully elucidated. It has been suggested that NE can increase neurogenesis by increasing Fgf2 release. Fgf2 is a trophic factor, primarily synthesized by astrocytes that can enhance the proliferative activity and the migratory properties of astrocytes and neuronal precursor cells. Indeed, it has been shown that IP injections of clenbuterol, a β2AR agonist in rats leads to a significant increase in Fgf2 mRNA levels in the hippocampus. Indeed, we found a significant reduction in Fgf2 gene expression in the DG in Ts65Dn mice. Interestingly, formoterol treatment caused a 20% and 80% increase in mRNA levels of this gene in the Ts65Dn and 2N mice respectively (FIG. 15).

The fact that we found significantly higher number of astrocytes in DG of Ts65Dn mice without a corresponding increase in Fgf2 gene expression suggests that the decrease in Fgf2 gene expression in these mice may be much more severe than those observed in 2N mice. Our data are supported by a recent study showing that increasing Fgf2 levels in the brain of mouse models of AD can significantly improve cognitive function and increase the rate of neurogenesis in the DG of the hippocampus.

Taken together, our data suggests that, through improving neurogenesis, increasing dendritic complexity, and thus synaptic strength, β2AR agonists can significantly improve contextual learning in the Ts65Dn mouse model of DS. This supports the idea that improving β2 signaling might be an attractive strategy in treating cognitive disabilities in people with DS. It has recently been shown that increasing brain NE levels can also reduce the severity of amyloid pathology in mouse models of AD. Since all adults with DS will eventually develop AD-related pathology, these findings suggest that NE-based therapy can potentially improve cognitive function in children and reduce the severity of amyloid pathology in adults with DS. The fact that formoterol has already been used for many years in humans, should further encourage exploration of this possibility and potentially expedite the use of this or others β2AR agonists to improve cognitive function in children and adults with DS.

Methods

Mice. Adult (5-6 month) male Ts65Dn mice (B6EiC3Sn.BLiA-Ts (17<16>)65Dn/DnJ, stock number: 005252) and gentler- and age-matched 2N controls (B6EiC3Sn.BLiaF1/J, stock number: 003647) were used (Jackson Laboratory). All experiments were approved by the Committee on Animal Research at the Veterans Affairs Palo Alto Health Care System. All animals were group-housed on a 12-hour light/dark cycle and fed ad libitum.

Pharmacological Treatments. To reduce the peripheral effects of formoterol, each formoterol injection (Tocris) was preceded by nadolol (Tocris) treatment. For details on methods of drug injections see FIG. 16.

Cardiovascular and respiratory system monitoring. Peripheral effects of fomoterol were assessed using MOUSEOX® Small Animal Vital Signs Monitor (Starr). The monitor was attached to a collar clip with an LED sensor to enable recordings in free-moving mice. To minimize stress before recording, the collar clip was attached to each animal. After five minutes, heart rate, respiratory rate, and oxygen saturation were recorded using MOUSEOX® 6.3.13 for 10 minutes.

Behavioral Testing a) Open Field Activity. Prior to testing, the mice were handled for five days for habituation. Thereafter, the mice were injected with nadolol and, after one hour, with either saline or formoterol. Four hours later, the mice were tested for open field activity. The open field arena (450 mm×450 mm) had visual cues on the walls. Each mouse was placed in the center of the arena and is movements were recorded for fifteen minutes using a CCD-camera (DM-CO-S20SIE). The arena was cleaned after each session. The velocity, total distance traveled, and the time spent in the peripheral 50% versus central 50% area of the arena (bouts) for each mouse were quantified and analyzed using TopScan Lite (Clever Sys).

b) Fear Conditioning. Since no abnormalities have been found in cued learning in Ts65Dn mice, we only tested contextual learning for this study. The fear conditioning tests were done using four FreezeScan chambers (Clever Sys) on days 4 and 5 after the start of the open field-testing. On day 4 (Training Day), all mice were injected with nadolol and then, after one hour, with either saline or formoterol. Four hours later, the mice were placed in the fear-conditioning chamber and their baseline activity was recorded for three minutes. At the end of this period, each mouse was exposed to five shocks (2 seconds each, 0.5 mA) with inter-trial intervals of 80 seconds. Twenty-four hours later, the mice were injected again, similar to the Training Day, and returned to the same fear-conditioning chamber for five minutes and their activity was recorded. Freezing was defined as a lack of movement for 3 frames (29 frames/s).

Postmortem Analysis. Postmortem analyses were done in two groups of naive and treated mice:

1) Naive Mice. Adult 2N and Ts65Dn mice were sacrificed using IP injection of sodium pentobarbital (200 mg/kg), trans-cardially perfused with saline, and brain was extracted. The left hemisphere was frozen for gene expression studies, ELISA, and Western blotting. The right hemisphere was fixed in paraformaldehyde overnight at 4° C. followed by dehydration in 30% sucrose and freezing on dry ice. This was followed by embedding each brain in OCT (Sakura) and storing in −80° C.

a) Synaptosome Preparation.

Hippocampi (n=12 mice per genotype, experiments repeated twice) were collected, pooled (3 hippocampi per sample), and homogenized in homgenization buffer (HB; 0.32 M sucrose, 10 mM Tris, 1× Sigma phosphatase inhibitor cocktail 2 and 3, 1× Roche Complete protease inhibitor tablet). The homogenate was centrifuged and the supernatant was run on successive sucrose gradients, to isolate the enriched synaptosomal fraction (ESF). ESFs were resuspended in lysis buffer (1% Trion, 1% NP40, 0.1% SDS, 0.5% Sodium-deoxycholate, 1× Roche Complete protease inhibitor cocktail, 1× Sigma phosphatase inhibitor cocktail 2 and 3, 2 mM PMSF in DPBS), and lysed, centrifuged, and the supernatant was collected and loaded onto 4-12% Bis-Tris gels (Invitrogen), separated by electrophoresis and tansferred to polyvinylidene fluoride membranes. Membranes incubated with a β2AR antibody in TBST overnight, washed and incubated with goat HRP-conjugated antibody (Millipore) in TBST. Immunoreactivity was detected using Immuno-Star Western Chemiluminescence Kit (BioRad), and band density was measured using FIJI (NIH).

b) Rapid Golgi Staining. A different group of adult Ts65Dn (5-6 months old) and 2N mice were sacrificed as described above, and their brains were immediately extracted and placed in Rapid Golgi Solution (15 ml per brain, Cornell Center for Technology Enterprise) at RT. Ten days layer, the brains were washed, dehydrated and cut (150 μm) using a vibratome (Leica CM 1950). All sections were mounted and coated with 50% sucrose. After drying for 72 hours at RT, the sections were rinsed in water and incubated for 10 minutes in the Golgi intensification solution supplied with the kit. The sections were dehydrated and cover-slipped.

c) ELISA Studies. An ELISA kit (Enzo, ADI-900-067) was used for cAMP quantification. The DG region of the hippocampus was punched out using a glass tube under a dissection microscope (Evolution xR6) at −30° C. and stored. The samples were ground to a fine powder under liquid nitrogen and the resulting samples were mixed with 10 volumes of 0.1 M Hcl followed by centrifugation according to the manufacturer's instructions. The total protein levels were quantified using a micro BCA protein assay kit (23235, Thermo) and spectrophotometer (Fisher) with absorbance at 562 nm.

2) Treated Mice At the end of behavioral analyses, the mice were injected IP with either nadolol alone or nadolol with formoterol for another 10 days. At the end of this period, all mice were anesthetized, perfused, and the brain was extracted. The right hemisphere from each brain was fixed in 4% paraformaldehyde followed by dehydration. The methodology for staining has been published before. The frozen hemispheres were cut coronally at 70 μm using a cryostat (Leica CM 1950), placed in cryoprotectant solution (25% ethylene glycol, 25% glycerol and 0.05M sodium phosphate buffer), and stored at −20° C. The left hemisphere was flash frozen and used for gene expression studies.

a) Immuno-Staining:

Before all staining(s), to inhibit endogenous peroxidase, 70-μm-thick floating sections were pre-incubated in 0.5% $H_2O_2$ in 50% methanol for 30 minutes at RT. This was followed by pre-incubating the sections in 0.1% triton and 10% normal serums(s) (NS, Vector Labs) for 1 hour at RT. This was followed by incubation in primary antibodies overnight at RT. We used antibodies against synaptophysin (SVP-38, Sigma, S5768), β2AR (SC596, Santa Cruz), GFAP (1:5000; Dako, Z033429), DCX (1:500, sc-8066, Santa Cruz), and c-Fos (1:800; Santa Cruz sc-52). For DCX staining the sections were kept in pre-warmed (37° C.) for 30 minutes before staining. This was followed by incubation in secondary antibodies that were diluted in 0.1% triton and corresponding 1% NS. The sections were then incubated in ABC Lite (1:1000, Vector) for 1 hour. Staining was terminated by incubating in DAB (0.66 mg/ml in tris-HCl) for 5-10 minutes. Finally, the sections were washed, dehydrated and mounted.

b) Synaptophysin-β2AR Co-Localization.

Twenty sections were used for this staining. The sections were incubated overnight in a rabbit antibody against β2AR (1:1000). Later, the sections were incubated in a biotinylated anti-rabbit (1:200; Vector) for 1 hour followed by incubation in streptavidin-conjugated Texas Red (Vector) for 1 hour. The sections were incubated with synaptophysin antibody (1:40, 000) for 30 minutes. The sections were then incubated with biotinylated anti-mouse (1:650, Jackson ImmunoResearch) for 30 minutes and then with ABC (1:1000) for 1 hour. The synaptophysin staining was visualized using tyramide signal amplification (TSA)-Cy3 (PerkinElmer). Sections were examined a confocal microscopy (Zeiss LSM 510). Excitation was 561 nm laser for both, and emission filters for Cy3 and Texas Red were NFT565 and LP575, respectively.

c) BrdU.

To identify proliferating cells, we used 5-bromo-2'-deoxyuridine (BrdU, Sigma). It was dissolved in PBS, filtered, and kept at 4° C. till use. After 15 days of treatment, each mouse was injected IP daily (50 mg/kg) with BrdU solution for 5 days. Thereafter, on day 21, all mice were anesthetized and transcardially perfused with ice-cold saline. The entire brain was immediately removed and the two hemispheres were separated. The left hemisphere was fixed overnight, cut, and stored. Sections were stained using BrdU antibody (1:1000; Millpore, MAB 4072) followed by incubation with biotinylated anti-mouse (1:20,000; Jackson), both for 1 hour. This was followed by incubation of sections in ABC.

Morphometry and Image Analysis

1) BrdU Cell Count.

Stereo-Investigator (MBF) was used to quantify the total number of BrdU-positive cells in the entire septo-temporal extent of DG. Following the outlining of the DG area at 4×, each positive profile was identified using a 100× oil objective. Unbiased stereological methods were used to determine the total number of BrdU-immunoreactive-profiles throughout the hippocampus. A Nanozoomer system (Hamamatsu 2.0 RS) was used to capture images of the entire slide in each case. High magnification images were captured using the Nanozoomer and stored.

2) Determination of Dendritic Tree.

Golgi-stained 150 μm-thick-sections were used to quantify the extent of dendritic arborization in the ML of DG using Neurolucida. 10-15 DGCs per mouse were traced using 100× oil objective.

3) Image Analysis Methods.

a) Synaptophysin.

To examine synaptic load in the DG of the hippocampus, we examined the overall optical density of immunostaining for synaptophysin in a total of 500 images, randomly chosen from the entire polymorphic layer of the hippocampus, and captured at 100× (1280×1200 pixels) using Image Pro Plus (MediaCybernetics).

b) GFAP Load Quantification.

Images throughout the entire septo-temporal axis of the hippocampus were captured using an analogue camera (Cohu) and digitized (10×). The z-axis on each slide was video recorded by moving from top to bottom of each field. The generated video files were decompressed using ImageJ. We performed extended depth of field correction on each video file. As a result, the most focused pixels it each image were transformed to a new composite picture, bringing all GFAP-positive-profiles to the same plane. Based on the optical density of each pixel, a mask was automatically generated. All images were automatically analyzed using Image Pro Plus.

c) GFAP-Positive-Profiles Localization Analysis.

Separate high-resolution (4076×3116 pixels) images were captured using 20× objective (Nikon, Eclipse 8oi) and stored. The location of each GFAP profile in the ML of the DG was quantified by measuring the distance between each profile and an arbitrary line drawn parallel to the DGC region (FIG. 14).

d) β2AR Immunoreactivity Quantification.

High-resolution images (4076×3116 pixels) were captured using Nikon DS-Ri1 digital camera attached to microscope. Using Image-Pro Plus, the images were de-convoluted and a mask was made to cover the immunoreactivity of β2 staining in each image (FIG. 4D). The total area covered by the mask was quantified in each image as percentage.

Gene Expression Studies.

The left hemisphere of each brain was placed in an aluminum box and snap frozen in liquid nitrogen and stored at −80° C. till use. The brain samples were sectioned coronally at 300 μm thickness. The DG and cerebellum were punched out using a 0.6 mm thick glass tube at −25° C. Total RNA was isolated using Trizol, and treated with DNAse I (Life Technologies). The following primers (IDT) were used: B-actin: 5'-AAATCGTGCGTGACATCAAA-3' (F) (SEQ ID NO: 1): AAGGAAGGCTGGAAAAGAGC (R) (SEQ ID NO: 2), Gapdh: TGCACCAACTGCTAAGC (F) (SEQ ID NO: 3): GGCATGGACTGTGGTCATGAG (R) (SEQ ID NO: 4), Fgf2: 5'-CACCAGGCCACTTCAAGGA-3' (F) (SEQ ID NO: 5): 5'-GATGGATGCGCAGGAAGAA-3' (SEQ ID NO: 6). Initial cDNA quantity and cycle threshold (CT) for each gene of interest was normalized to the geometrical average of the two normalizers (B-actin and Gapdh). The resulting values were normalized to the values of a 2N mouse, amplified in all plates.

Statistical Analysis.

All data are presented in terms of mean±standard error of the mean (s.e.m). The Student t-test was use to compare naive 2N and Ts65Dn mice. We used ANOVA (STATISTICA 6.0, StatSoft) to assess the effects of genotype and treatment on each of the parameters that were quantified. This was followed by a Fisher's least significant difference post-hoc analysis. Differences were considered to be statistically significant when $P<0.05$.

Acknowledgements

The work leading up to the present invention supported by pasts from the Down Syndrome Research and Treatment Foundation (DSRTF) and Alzheimer's Association. The support provided by the MIRECC and WRIISC programs at the VA Palo Alto Health Care System is highly appreciated.

Legends

FIG. 9.

Schematic representation of genes triplicated in DS and in the Ts65Dn mouse that play a role in nervous system abnormalities. Among a total of 327 genes on HSA21, around 143 (43%) are also found in three copies in Ts65Dn mice (Alford et al., Blood, 115: 2928-2937, 2010). All genes found on Down Syndrome Critical Region (DSCR) are also found in Ts65Dn mice. Genes marked in green are those that are triplicated Ts65Dn mice while those marked in red are not triplicated in Ts65Dn mice.

FIGS. 1A-1G.

Volume of the hippocampus and different layers of the DG in naive adult Ts65Dn mice and their controls. (FIG. 1A) Schematic representation of the hippocampus region and the sub-regions of the DG. Unlike the hippocampus volume (FIG. 1B) (2N=11.552±0.70 mm$^3$, n=5, Ts65Dn=10.583±0.51 mm$^3$, n=5, t-value=1.115, P=0.297), we found a significant reduction in the volume of the DGC layer (FIG. 1C) (2N=0.542±0.04 mm$^3$, n=5, Ts65Dn=0.419±0.03 mm$^3$, n=5, t-value=2.574, *P=0.032) and ML (FIG. 1D) (2N=4.057±1.93 mm$^3$, n=5, Ts65Dn=3.256±0.22 mm$^3$, n=5, t-value=2.708, **P=0.026) in Ts65Dn mice compared to 2N mice. FIG. 1E) The status of dendrite arborization of DGCs in the ML of the DG in naive Ts65Dn mice and 2N mice. Each individual neuron was separately traced and then superimposed at the level of the cell body. Visualization of order of dendritic arborization and quantification of the total length of dendrites in relationship to the order of branching. (FIG. 1F) We found a significant reduction in the length of 3rd order dendritic branching of DGCs in Ts65Dn mice (*P=0.040). (FIG. 1G) A significant reduction in the average length of dendrites in Ts65Dn compared with 2N mice (2N=46.99±4.50 μm, n=5, Ts65Dn=34.65±1.55 μm, n=5, t=3.01, **P=0.016) was also detected.

FIGS. 2A-2B.

Quantification of cAMP levels in the DG of naive Ts65Dn and 2N mice. (FIG. 2A) Location of micro-punch through the DG of the Hippocampus that was analyzed here. (FIG. 2B) We found a significant reduction in cAMP levels in DG area of Ts65Dn mice compared with 2N mice. (2N=10.540±0.34 pM/ml, n=3, Ts65Dn=8.182±0.31 pM/ml, n=5, t=4.820, **P=0.002).

FIGS. 3A-3H.

Figure 3G:
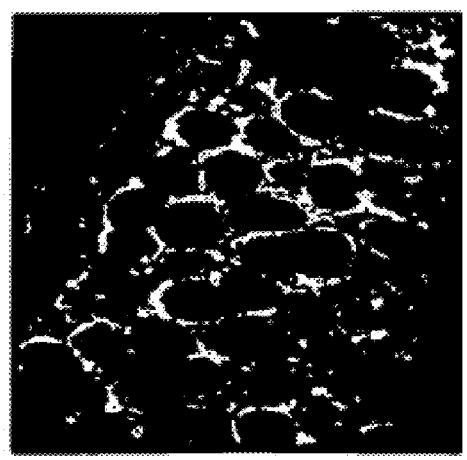
Figure 3H:
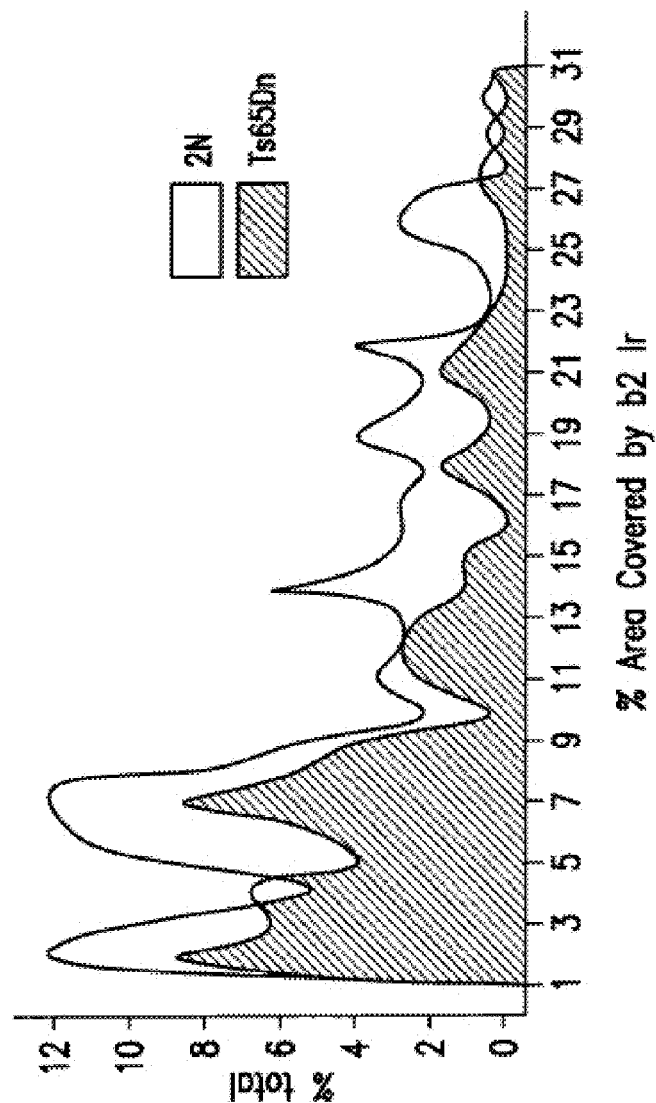

Immunocytochemical visualization of synaptosphysin (FIG. 3A) and β2AR (FIG. 3B) in DGCs. FIG. 3C) We found that the majority of synaptophysin-stained puncta in DGC's soma and cell membrane also contained β2AR immunostaining. Images taken from DGC cell bodies (FIG. 3D) were processed for deconvolution (FIG. 3E) and a mask (FIG. 3F) automatically generated by Image-Pro Plus was superimposed on each image. FIG. 3G) This was followed by quantification of the area occupied by the mask. FIG. 3H) Quantification of the immunoreactivity for β2ARs showed a significant shift to higher values in adult Ts65Dn mice compared with 2N controls ($X^2$=91.343, p<0.0001), (2N-nadolol: n=9, 2N-formoterol: n=7, Ts65Dn-nadolol: n=6, Ts65Dn-formoterol: n=6) Scale bar=10 μm (FIGS. 3A-3C) and 20 μm (FIGS. 3D-3G). β2IR, β2 Immunoreactivity.

FIGS. 10A-10B.

Effects of formoterol treatment on vital signs of Ts65Dn and 2N mice. (FIG. 10A) No significant effects of formoterol were found on the heart rate (P=0.369, F=0.839). Similarly, ANOVA showed no significant effects of genotype (P=0.104, F=2.852) on the heart rate in treated mice (heart rate measured in pulse per minute: 2N-nadolol=660.981±35.86, n=9, 2N-formoterol=638.440±44.77, n=7, Ts65Dn-nadolol=677.740±40.11, n=6, and Ts65Dn-formoterol=672.620±36.58, n=6). (FIG. 10B) No significant effects of formoterol were found on the respiratory rate (P=0.770, F=0.09). However, we found significant effects of genotype on respiratory rate in treated mice (P=0.002, F=11.82) (respiratory rate per minute: 2N-nadolol=165.560±5.22, n=9, 2N-formoterol=165.890±5.99, n=7, Ts65Dn-nadolol=185.700±5.34, n=6, and Ts65Dn-formoterol=189.090±8.40, n=6). Fisher's post-hoc analysis also showed significantly higher respiratory rate in Ts65Dn mice and their 2N counterparts (*P=0.028). Similarly, Ts65Dn mice treated with formoterol also showed significantly higher respiratory rate compared to their 2N mice (**P=0.018).

FIGS. 4A-4C.

(FIG. 4A) The effects of formoterol treatment on oxygen saturation in 2N and Ts65Dn mice. Oxygen saturation was quantified in each mouse using an infrared detector. We found no effects of either genotype (P=0.120, F=2.595) or treatment (P=0.259, F=1.335) on oxygen saturation (percent O2 saturation: 2N-nadolol: 92.527±0.54, n=9, 2N-formoterol: 93.221±0.36, n=7, Ts65Dn-nadolol: 90.993±1.01, n=6, Ts65Dn-formoterol: 92.205±1.31, n=6). (FIG. 4B) Using fear conditioning, contextual learning was quantified one day after initial training. There was a significant effect of genotype (P<0.0001, F=55.95) and treatment (P<0.0001, F=25.41) on freezing behavior (duration of freezing in number of seconds per minute: 2N-nadolol=46.761±3.09, n=15, Ts65Dn-nadolol=19.28±4.79, n=11). Fisher's post-hoc analysis showed a significant reduction in freezing behavior in Ts65Dn mice treated with nadolol compared to their 2N counterparts (*P=0.00001). Although we found a significant difference between the 2N and Ts65Dn groups treated with formoterol (*P=0.000001) that was due to positive effects of formoterol on 2N mice. Compared to Ts65Dn mice treated with nadolol, those treated with fomoterol showed a significant improvement in freezing (Ts65Dn-formoterol=34.040±3.66 seconds per minute, n=7, P=0.0011). (FIG. 4C) The effects of formoterol on freezing behavior during the first 5 minutes of exposure to the context. There was a significant reduction in freezing in Ts65Dn mice treated with nadolol compared with their corresponding 2N group (P<0.01, and ***P<0.0001).

FIGS. 5A-5D.

The effects off formoterol treatment on mean velocity in TS65Dn and 2N mice. (FIG. 5A) ANOVA showed significant effects of both genotype (*P<0.001, F=12.72) and treatment (P=0.005, F=8.97) on velocity. Fisher's post-hoc analysis showed formoterol treatment led to a significant reduction in velocity in Ts65Dn mice (P=0.0014) and a modest but not significant decrease in velocity in 2N mice (P=0.468) (velocity in mm/s: 2N-nadolol=31.465±2.74, n=15, 2N-formoterol=27.523±1.72, n=7, Ts65Dn-nadolol=52.965±4.59, n=12, Ts65Dn-Formoterol=33.682±3.85, n=7). (FIG. 5B) A similar effect was found in the total distance travelled in 10 minutes (ANOVA, genotype: p<0.001, F=12.35, and treatment: P=0.004, F=9.38). Fisher's post-hoc analysis showed formoterol treatment led to a significant reduction in the distance travelled in Ts65Dn mice (P=0.001) and a modest decrease in 2N mice (P=0.465) (total distance travelled in meters: 2N-nadolol=18.233±1.48, n=15, 2N-formoterol=15.989±0.96, n=7, Ts65Dn-nadolol=30.424±2.70, n=12, Ts65Dn-formoterol=19.224±2.02, n=7). (FIGS. 5C-5D) Quantification of the velocity of each mouse within the first 10 minutes of exposure to the open field arena. Formoterol treatment caused significant reduction in the velocity of Ts65Dn mice throughout the 10 minute exposure to the open field arena.

FIGS. 11A-11C.

The total number of crossings (bouts) from the central 50% area to the peripheral 50% and vice versa was automatically calculated in the open field arena (FIG. 11A). Bouts are defined as the number of crossings from the peripheral 50% area to the central 50% area and vice versa (open field arena) (FIGS. 11B-11C). The ANOVA test showed a significant effect of genotype (central area: P=0.005, F=8.794 and peripheral area: P=0.011, F=7.254) and treatment (central area: P=0.005, F=9.150 and peripheral area: P=0.005, F=8.709) on the total number of bouts. Fisher's post hoc analysis showed a significant increase in the number of bouts from the central 50% area to the peripheral 50% area and vice versa in Ts65Dn mice (**P=0.002 for central and *P=0.007 for peripheral). Formoterol treatment led to a significant reduction in the number of bouts in both central and peripheral 50% areas in Ts65Dn mice (central area: *P=0.011 and peripheral area: *P=0.017) (central area: 2N-nadolol=39.46±4.96, n=15; 2N-formoterol=27.57±4.06, n=7, Ts65Dn-nadolol=60.25±4.95, n=12, Ts65Dn-formoterol=49.14±4.86, n=7. Peripheral area: 2N-nadolol=45.00±5.68, n=15; 2N-formoterol=29.71±5.03, n=7, Ts65Dn-nadolol=67.00±6.54, n=12, Ts65Dn-formoterol=43.28±5.63, n=7).

FIGS. 6A-6C. (FIG. 6A) Formoterol treatment restored synaptic density in the DG in Ts65Dn mice Quantifying the percentage of area covered by synaptophysin staining showed a significant effect of genotype on synaptophysin (**P=0.008, F=8.455). Fisher's post hoc analysis showed a significant decrease in the synaptic load in adult Ts65Dn mice compared with their corresponding 2N group (2N-nadolol=27.40±11.00%, n=6, and Ts65Dn-nadolol=21.50±1.00%, n=7, P=0.008). Treatment with formoterol led to a significant increase in synaptophysin load in Ts65Dn mice (Ts65Dn-nadolol=21.50±1.00% and Ts65Dn-formoterol=25.80±2.00% n=7 *P=0.035). No significant effects of formoterol were found in the 2N group (2N-nadolol=27.40±11.00% and 2N-formoterol=28.50±2.00% P=0.627). (FIG. 6B) We found a significant reduction in the density of c-Fos-positive DGCs in Ts65Dn mice compared with 2N mice (2N-nadolol=179.30±22.4 cells/mm$^2$, n=6 and Ts65Dn-nadolol=109.42±13.0 cells/mm$^2$, n=7, P=0.0072). Interestingly, treating Ts65Dn mice with formoterol led to a significant increase in the density of c-Fos-positive DGCs in these mice compare to 2N controls (Ts65Dn-formoterol=189.60±14.60 cells/mm$^2$, n=6 2N-formoterol=151.25±15.20 cells/mm$^2$, n=6, *P=0.00014). Two-way ANOVA showed a significant interaction between genotype and treatment (F=10.706, P=0.0035) on the density of c-Fos-positive DGCs. (FIG. 6C) Quantifying the density of c-Fos-positive cells in the DGC region across the rostro-caudal axis of the hippocampus in Ts65Dn mice showed that formoterol led to a significant increase in the density of c-Fos positive cells throughout along the rostro-caudal axis the hippocampus in these mice (**P<0.001, and *P<0.05, the x-axis shows section number along the rostro-caudal axis of hippocampus).

Figure 12B:
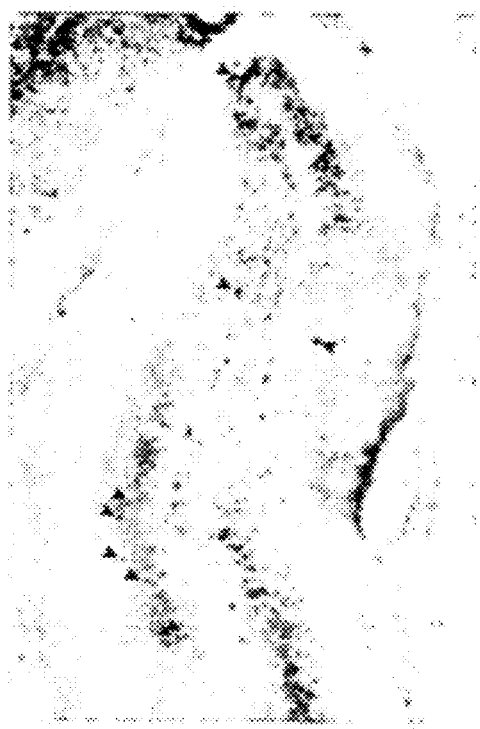
FIGS. 12A-12D. Immunocytochemical visualization of c-Fos-positive neurons in the DGC layer in Ts65Dn and 2N mice, treated with either nadolol alone or nadolol and formoterol. A drastic decrease in the number of c-Fos-positive DGCs was found in nadolol-treated Ts65Dn mice (FIG. 12B) compared with 2N controls (FIG. 12A). Furthermore, formoterol administration led to a significant increase in the number of c-Fos-positive cells in Ts65Dn mice (FIG. 12D). Scale bar=100 μm.
Figure 12D:
Figure 12A:
Figure 12C:

FIGS. 12A-12D. Immunocytochemical visualization of c-Fos-positive neurons in the DGC layer in Ts65Dn and 2N mice, treated with either nadolol alone or nadolol and formoterol. A drastic decrease in the number of c-Fos-positive DGCS was found in nadolol-treated Ts65Dn mice (FIG. 12B) compared with 2N controls (FIG. 12A). Furthermore, formoterol administration led to a significant increase in the number of c-Fos-positive cells in Ts65Dn mice (FIG. 12D). Scale bar=100 μm.

FIGS. 7A-7D. (FIG. 7A) Immunocytochemical visualization of GFAP in the DC of a 2N mouse (Scale bar: 20μ). GFAP-positive profiles were mainly detected among the DGC somata and in both polymorphic and the ML of the DG. DGC deflate granule cell; ML, molecular layer; PML, Polymorphic Layer. (FIGS. 7B-7D) Frequency distribution of distances of GFAP-positive profiles from the DGC area. Although we found no differences in the frequency distribution of the distance from the DGC layer between the 2N and Ts65Dn mice treated with nadolol ($X^2$=3.46, P=0.983), a significant increase in distance of astrocytes was observed in Ts65Dn treated with formoterol ($X^2$=21.103, P=0.032). No significant effects of formoterol were found in the 2N group ($X^2$=16.90, P=0.110).

FIGS. 13A-13B. Immunocytochemical visualization of GFAP positive astrocytes in the DG of 2N (FIG. 13A) and a Ts65Dn (FIG. 13B) mouse. A drastic increase in the density GFAP-positive-profiles was found in the ML and the PML regions of the DG in Ts65Dn mice. ML, Molecular Layer; DGC, Dentate Granular Cell layer; PML, Polymorphic Layer, Scale bar=300 μm.

FIGS. 8A-8H. (FIGS. 8A-8C) BrdU-positive profiles (arrows) in the DG of a 2N mouse [Scale bar=300μ (FIG. 8A), 100μ (FIG. 8B), 80μ (FIG. 8C)] (FIG. 8D) The total number of BrdU-positive profiles in the DG was 37% lower numbers in Ts65Dn mice compared to 2N controls. Formoterol increased the number of BrdU-positive cells in DG in Ts65Dn mice and their 2N controls. ANOVA showed significant effects of treatment (P=0.018, F=6.749) and no effects of genotype (P=0.762, F=0.094) on number of BrdU-positive profiles. Post-hoc test showed that fomoterol treatment caused a significant increase in the number of BrdU-positive profiles in Ts65Dn mice (*P=0.031). (2N-nadolol=3,161.390±900, n=5, 2N-formoterol=5,145.970±1051, n=6, Ts65Dn-nadolol=2,133.290±491, n=5 and Ts65Dn-formoterol 5,539.600±1301). (FIG. 8E) DCX-positive neurons in the DG of a 2N mouse; Scale bar=170 μm. (FIG. 8F) The number of DCX-positive DCGs in 2N and Ts65Dn mice. ANOVA showed significant effects of genotype (P=0.0001, F=21.50) and no effects of treatment on the number of DCX-positive cells. Post-hoc analysis showed a significant (P=0.004 2N-nadolol=5391.36±744, n=6; Ts65Dn-nadolol=2837.79±500, n=6) decrease in the number of DCX-positive neurons in Ts65Dn mice compared with 2N mice. No significant effects of formoterol were found in either genotype (2N-formoterol=5148.91±350, Ts65Dn formoterol=2619.28±508). (FIG. 8G) The order of branching is Ts65Dn and 2N mice. (2N-nadolol=2.05±0.12, n=6, 2N-formoterol=1.66±0.08, n=6, Ts65Dn-nadolol=1.58±0.08, n=7, Ts65Dn-formoterol=2.24±0.10, n=8). A significant interaction of genotype and treatment (P=0.0001, F=26.06) was found on the order. Post-hoc showed a significant reduction in the order in Ts65Dn compared with 2N (P=0.004). Furthermore, a significant positive effect of formoterol was found to Ts65Dn mice (***P=0.000075). Interestingly, a significant reduction was found in 2N-formoterol compared with 2N-nadolol (*P=0.018). (FIG. 8H) The increase in the dendritic span in the fomoterol-treated Ts65Dn mice has been clearly demonstrated.

FIG. 14. Method of quantification of the distance between an arbitrary line drawn in the middle of the DGC layer and the position of GFAP-positive profiles (arrows depict the distance between the DGC layer and individual astrocytes). ML, Molecular Layer; DGC, Dentate Granular Cell layer; PML, Polymorphic Layer, Scale bar=150 μm.

GFAP load in the molecular layer of the dentate gyrus in 2N and Ts65Dn mice treated with nadolol or formoterol. Unlike treatment, a significant effect of genotype was found on GFAP load in mice tread with either nadolol or formoterol.

FIG. 15. We found a significant increase in gene expression for Fgf2 in micro-punches through the DG of Ts65Dn mice. ANOVA test showed significant effects of genotype (P=0.015, F=6.099) and no effects of treatment (P=0.292, F=1.125) on Fgf2 gene expression. Post-hoc test showed significant difference between formoterol treated 2N and Ts65Dn mice (*P=0.042). (2N-nadolol=1.000±0.41, n=22; 2N-formoterol=1.790±0.75, n=17; Ts65Dn-nadolol=0.344±0.07, n=16; Ts65Dn-formoterol=0.423±0.05, n=22).

Figure 16:
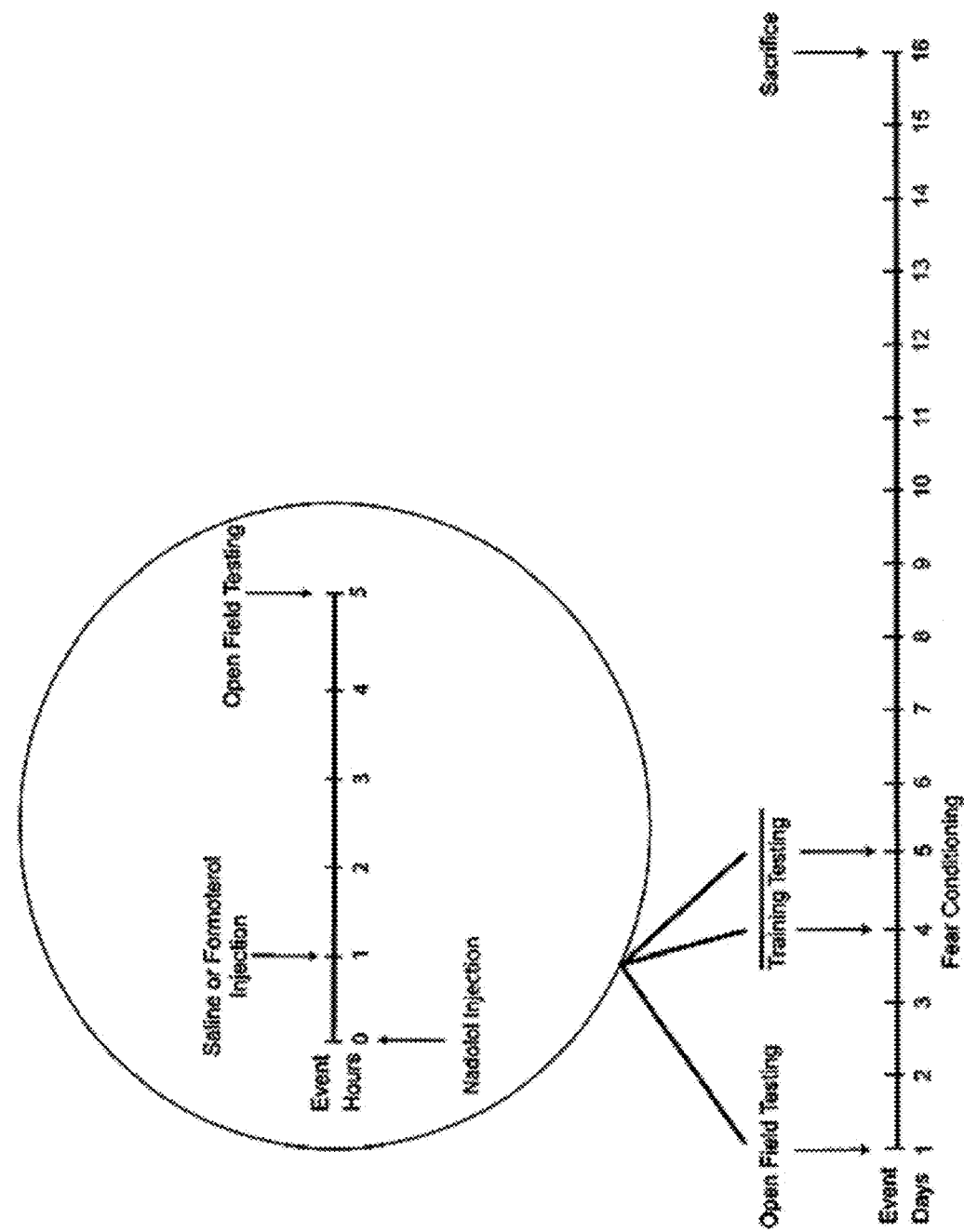
FIG. 16 illustrates the strategy used for performing IP injections of βAR agonist and antagonist and behavioral testing.

FIG. 16. Strategy used for performing IP injections of βAR agonist and antagonist and behavioral testing. Nadolol is a β1 and 2 antagonist that does not cross the BBB. All mice were initially injected intraperitoneally (IP) with nadolol (10 μl/g, 5 mg/kg) (N1892, Sigma-Aldrich). One hour later, the mice were randomly divided into two groups and were injected with either formoterol (10 μl/g, 2 mg/kg) or 0.9% saline (10 μl/g). Four hours later, the mice were tested for cardiovascular and respiratory system effects, open field activity, or fear conditioning. The process started with open field-testing on day 1 followed by fear conditioning on days 4 (training) and 5 (testing). At the end of behavioral analyses, the daily IP injections of nadolol or formoterol were continued for another 10 days. At the end of this period, all mice underwent cardiac perfusion (day 16).

As noted above, in treating the Ts65Dn mouse model of DS, generally one or more β2 agonists may be administered in conjunction with one or more β1-blockers, also known as β1-adrenergic antagonists. Specifically, since cardiac complications are the most common cause of death in people with DS, it is preferable to administer one or more β1-blockers first in order to preclude or minimize, peripheral agonism of β1 adrenergic receptors by subsequently administered β2 agonists where it is known or determined that the one or more β2 agonists administered exhibit some β1 agonism.

The β2 agonists and β1 antagonists or blockers may be administered by inhalation or by injection, for example, subcutaneously. Generally, individual human doses of the one or more β2 agonists range from about 2 to 100 mg per administration. It is preferable, however, that the individual does be from about 5 to 30 mg per administration. The β2 agonists may be administered in sterile saline or dextrose saline solution, for example 0.9% by weight sterile aqueous saline solution. Any common aqueous-based solvent for injectable pharmaceuticals may be used. A typed concentration of the one or more β2 agonists in aqueous based solvent in about 10 μl/g.

The compounds or compositions of the present invention may also be administered by inhalation, such as with a nebulizer inhaler or a dry powder inhaler. See U.S. Pat. No. 7,569, 586, which is incorporated herein in the entirety. The compounds or compositions of the present invention may be formulated and administered as described in U.S. Pat. No. 7,569,586, however, without using the additive drugs, such as muscarinic antagonists, antihistamines and steroidal anti-inflammatory compounds, which would otherwise be used in treating pulmonary disorders, such as COPD (chronic obstructive pulmonary disorder) or asthma. However, medically inactive additives and diluents many be used as described in U.S. Pat. No. 7,569,586

Single or multiple administrations may be used for the one or more β2 agonists. For example, during a course of treatment, a steady state level of β2 agonist in a patient over a period of time may be effected by use of multiple treatments in series. If such a treatment is used, the individual doses in the series are generally in the range of 5 to 30 mg per administration, and preferably from about 10 to 20 mg per administration. Specific examples are 11 mg, 12 mg, or 17 mg of one or more β2 agonists, such as formoterol, per administration.

The one or more β1-blockers are generally administered at from the same dosage level to up to twice the dosage level as the one or more β1-blockers. For example, dosages of from about 20 to 40 mg of β1-blocker may be administered per dosage. The one or more β1-blockers may also be administered singly or multiple times in concordance with β2 agonist administration.

For example, as an exemplary treatment for humans having DS, formoterol may be administered subcutaneously at a dosage level of 11.38 mg for a 70 kg human. The β1-blocker, nadolol, may be administered prior to or concurrent with formoterol in an amount of 28.45 mg per the same 70 kg human.

In accordance with the present invention, adult humans may be treated in order to increase cognition and increase dendritic complexity. Further, this may be done with minimal peripheral cardiac effects, which would normally occur with agonism of β1 adrenergic receptors.

Additionally, however, the present invention specifically contemplates the treatment of children having DS. Specifically, treatment of children at age 5 or older is advantageous in order to increase dendritic complexity of cells in dentate gyrus, for example, as early in human brain development as possible. The dosage levels described above may be used for both children and adults in both single and multiple treatments.

Specific exemplary combinations of the one or more β2 agonists are salbutamol and salmeterol, or terbuline and bambuterol, or procaterol and formoterol. However, as already noted, any single β2 agonist, such as formoterol, may be used in either single or multiple treatments in series.

Specific exemplary combinations of the one or more β1-blockers are nadolol and atenol, or Nadolol and betaxolol, or esmolol and metaprolol. However, as already noted, any single β1-blocker, such as nadolol, may be used in either single or multiple treatments in series.

Examples

An eight (8) year old child having DS, and having a body weight of 35 kg is treated multiple time in series with formoterol and nadolol in order to improve dendritic complexity and increase cognitive functions, and to preclude or minimize adult onset of AD brain pathology.

Over a period of 6 weeks, the child is treated as follows:
Child is subjected to contextual learning testing,
14 mg of nadolol is administered by subcutaneous injection (nadolol in 0.9% saline),
2 hours later, 6 mg of formoterol is administered by subcutaneous injection (formoterol in 0.9% saline) {nadolol/formoterol administration is conducted once or twice weekly},
Child is again subjected to contextual learning testing after the cessation of the treatment regime to determine the adequacy of treatment or whether further treatment is necessary. Improvements in test scores are indicative of treatment success.

Over a period of 10 years, the same child may, in the alternative, be treated as follows:
Child is subjected to contextual learning testing,
13 mg of nadolol is administered by subcutaneous injection (nadolol in 0.9% saline),
2 hours later, 7 mg of fomoterol is administered by subcutaneous injection (formoterol in 0.09% saline) {nadolol/formoterol administration is conducted once a month over a period of 10 years.
Child is again subjected to contextual learning testing at the end of each year during the duration of period to determine the adequacy of treatment or whether further treatment is necessary. Improvements in test scores are indicative of treatment success.

Contextual learning is a major part of learning and memory that fails in humans with DS. Contextual learning is also a reliable means of conducting memory assessment in mice. In fact, learning and memory in both humans and mice appears to be related to attention. For example, in studies with mice, mice that failed to pay attention to context, also failed to remember it.

Contextual learning is mediated by the hippocampus, and any problems with hippocampal structure, particularly the dentate gyrus, would lead to abnormalities in contextual learning.

Administration of the one or more β2 agonists to humans with DS, both adult and child, in accordance with the present invention has the additional advantage of reducing the severity of hyperactivity. Hyperactivity, in turn, may well be a sign of attention deficit, and addressing this additional problem helps to improve cognitive function.

Any accepted contextual learning tests used in the present invention to both assess baseline cognitive function and to measure or quantify improved cognitive function may be used. For example, the contextual learning test used may be based upon single task learning, multiple task learning or spatial contextual memory. Contextual learning test evaluations based upon spatial contextual memory are advantageous in assessing, for example, how well an individual is able to navigate a shopping mall, his or her neighborhood or a city transit or subway system as well as assessing any improvements in the ability to execute these tasks resulting from the treatment methods described herein.

An example of a simple spatial contextual learning test is contextual cuing, where humans learn to use repeated spatial configurations to facilitate a target search. A higher order spatial contextual learning test is serial learning, where humans learn to use subtle sequence regularities to respond more quickly and accurately to a series of events. See, for example, J. H. Howard Jr. et al, Neuropsychology, Vol. 18(1), January 2004, 124-134.

A particularly advantageous testing protocol that may be used is the Arizona Cognitive Test Battery (ACTB). See Edgin, J., et al. J. Neurodevelop. Disord. (2010) 2: 149-164. The ACTB has been developed specifically to assess the cognitive phenotype in DS, and includes various tests with various task demands and links with brain function. In more detail, tests are included for: 1) benchmarks, such as KBIT II verbal subscale and KBIT II non-verbal subscale IQ tests, 2) hippocampal function, 3) prefrontal function, 4) cerebellar function, 5) finger sequencing tasks, 6) NEPSY visuomotor precision and 7) simple reaction time.

A correlation of domain/test, test description and primary ability assessed in accordance with the ACTB is provided below:

| Domain/Test | Description | Primary Ability Assessed |
|---|---|---|
| 1) Benchmark KBIT-II verbal subscale KBIT-II nonverbal subscale | Points to pictures based on word or phrase Semantic or visuo-spatial pattern completion | Verbal comprehension Problem solving |
| 2) CANTAB spatial span | Touching boxes in order of Changing color on screen | Immediate memory for spatial-temporal sequence |
| 3) Prefrontal Modified dots task | Press button below a cat, shifts to new rule, press across screen for a frog, etc. | Inhibitory control working memory |
| 4) CANTAB IED | Forced-choice discrimination task with change in relevant dimension | Set-shifting |
| 5) Hippocampal CANTAB paired associates | Recall for hidden abstract patterns | Spatial associative memory |
| 6) Virtual computer-generated arena | Navigation of a virtual arena (via joystick) to find a hidden target | Spatial memory |
| 7) Cerebellar Finger-sequencing task | Sequences generated by tapping a number of fingers (1, 2, 3, 4) to a lever in succession | Motor sequencing |
| 8) NEPSY visuomotor precision | Follows two tracks with a pen | Visuo-motor tracking, hand-eye coord. |
| 9) CANTAB simple reaction time | Participants press button in response to a box presented on a screen | Motor response time and attention |

The above battery of tests are generally all performed in order to assess all major cognitive processes known to be affected by DS balanced by the practical need for testing under time constraints. The ACTB affords an advantageous manner of evaluating the effects of the present invention on individuals with DS.

Generally, the battery of tests are conducted with a test group of about 80 DS individuals, and a control group of about 80 DS individuals. The test group is treated with any of the treatment regimes described herein, and the control group is treated with placebo, such as a dextrose 5% saline solution by injection.

Additionally, the treatment regimes described above may be given individually, but the effects of the treatment regimes are analyzed using test groups of about 80 versus control groups of about 80 as described above.

Finally, U.S. Ser. No. 12/801,002, is specifically incorporated herein in the entirety, wherein the compounds and compositions described therein may be administered as described therein or herein and the effects thereof assessed as described herein. More particularly, combinations of any of the compounds and/or compositions as disclosed in U.S. Ser. No. 12/801,002, may be used in combination, as in mixed compositions or by joint administration, with the compounds and/or compositions of this application. In fact, in view of the disclosures of both applications, the treating physician may decide to use the compounds or compositions of U.S. Ser. No. 12/801,002, or those as disclosed herein or a mixture or combination thereof.

An improvement in cognitive function as defined herein as being at least a 10% and preferably at least a 20% score improvement, on at least one, and preferably two or more, of the tests listed in the ATCB, for example. Anyone of the domain/tests listed for the ATCB above may be included in assessing whether an improvement occurred. Testing may be conducted after treatment or during treatment to ascertain whether modifications in dosage or frequency of treatment is warranted.

Furthermore, the present invention also provides a method of inhibiting onset of adult AD brain pathology in a child having DS, which entails administering one or more β2 adrenergic receptor agonists to the child in an amount and with a frequency of administration effective to inhibit the onset.

Generally any non-invasive procedure many be used to both establish a baseline of brain pathology (existent or non-existent) from which baseline a treatment protocol is established. However, magnetic resonance imaging (MRI) is preferred for neuroimaging examination because it allows for accurate measurement of the 3-dimensional (3D) volume of brain structures, especially the hippocampus and related regions. Such techniques are well known as described in U.S. Pat. No. 6,490,472, which patent is incorporated herein in the entirety. Other techniques, such as fluorodeoxyglucose position emission tomography (FDG-PET) may also be used for neuroimaging.

Moreover, non-invasive optical imaging systems may also be used for monitoring early AD pathological events. See, for example, U.S. patent publication 2011/0286932, which is incorporated herein in the entirety. The technique described therein entails administration of a flourescent marker to a human (and for the present invention a DS human) for staining Aβ peptides, imaging the retina of the DS human with an optical imaging system, and examining the images for stained Aβ peptides in order to determine whether onset of AD brain pathology has occurred.

Additionally, test groups of about 80 individuals are used versus control groups of about 80 individuals. This treatment many also be used for treatment of single individuals in order to inhibit onset of adult AD brain pathologies in a child, or even in older individuals having AD.

The present invention may be practiced with modifications within the skill of the artisan without departing from the spirit and scope thereof.

What is claimed is:

1. A method of improving cognitive functioning in a human having Down syndrome, comprising administering an effective amount of a β2 adrenergic receptor agonist capable of crossing the human blood-brain barrier or a pharmaceutically acceptable salt thereof in combination with a β1 adrenergic receptor antagonist incapable of crossing the human blood-brain barrier or a pharmaceutically acceptable salt thereof to the human thereby improving the cognitive functioning of said human, wherein the β2 adrenergic receptor agonist is more selective for β2 adrenergic receptors than for β1 adrenergic receptors.

2. The method of claim 1, wherein said β2-adrenergic receptor agonist is short-acting, long-acting of ultra-long acting.

3. The method of claim 1, wherein said β2 adrenergic receptor agonist is formoterol or a pharmaceutically-acceptable salt thereof.

4. The method of claim 1, wherein said β2 adrenergic receptor agonist increases dendritic complexity in said human.

5. The method of claim 1, wherein said β2-adrenergic receptor agonist is administered orally or by injection.

6. The method of claim 1, wherein said β2-adrenergic receptor agonist is administered by inhalation.

7. The method of claim 1, wherein said β2-adrenergic receptor agonist and said β1-adrenergic receptor antagonist are administered by inhalation.

8. The method of claim 1, wherein the human is a child.

9. The method of claim 1, wherein the human is an adult.

10. The method of claim 1, wherein said β1 adrenergic receptor antagonist is nadolol.

11. The method of claim 1, which further comprises measuring the improved cognition by a contextual learning test.

12. The method of claim 11, wherein the improved cognition is measured by ATCB testing.

13. A method of inhibiting onset of adult Alzheimer's disease brain pathology in a child having Down syndrome, comprising administering a β2 adrenergic receptor agonist capable of crossing the human blood-brain barrier in combination with a β1 adrenergic receptor antagonist incapable of crossing the human blood-brain barrier to the child thereby inhibiting said onset of adult AD.

14. The method of claim 13, wherein the β2 adrenergic receptor agonist is formoterol or a salt thereof.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aaatcgtgcg tgacatcaaa                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggaaggct ggaaaagagc                                               20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcaccaact gcttagc                                                  17

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcatggact gtggtcatga g                                             21

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccaggcca cttcaagga                                                19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatggatgcg caggaagaa                                                19